US010195274B2

(12) United States Patent
Mumm et al.

(10) Patent No.: US 10,195,274 B2
(45) Date of Patent: Feb. 5, 2019

(54) METHOD OF MODULATING A CHIMERIC ANTIGEN RECEPTOR T CELL IMMUNE RESPONSE BY ADMINISTERING IL-10

(71) Applicant: ARMO BioSciences, Inc., Redwood City, CA (US)

(72) Inventors: John Brian Mumm, Los Altos Hills, CA (US); Ivan Ho Chan, Redwood City, CA (US)

(73) Assignee: Armo Biosciences Inc., Redwood City, CA (US)

( * ) Notice: Subject to any disclaimer, the term of this patent is extended or adjusted under 35 U.S.C. 154(b) by 0 days.

(21) Appl. No.: 15/926,118

(22) Filed: Mar. 20, 2018

(65) Prior Publication Data
US 2018/0207270 A1 Jul. 26, 2018

Related U.S. Application Data

(63) Continuation of application No. 15/165,918, filed on May 26, 2016, now abandoned.

(60) Provisional application No. 62/167,699, filed on May 28, 2015.

(51) Int. Cl.
| | |
|---|---|
| A61K 38/20 | (2006.01) |
| A61K 39/39 | (2006.01) |
| C07K 14/725 | (2006.01) |
| C07K 16/30 | (2006.01) |
| A61K 39/395 | (2006.01) |
| A61K 9/00 | (2006.01) |
| C12N 15/113 | (2010.01) |
| A61K 47/60 | (2017.01) |
| A61K 39/00 | (2006.01) |

(52) U.S. Cl.
CPC ...... *A61K 39/39558* (2013.01); *A61K 9/0019* (2013.01); *A61K 38/2066* (2013.01); *A61K 39/39* (2013.01); *A61K 47/60* (2017.08); *C07K 14/7051* (2013.01); *C07K 16/30* (2013.01); *C12N 15/1136* (2013.01); *A61K 2039/5158* (2013.01); *A61K 2039/55527* (2013.01); *C07K 2317/73* (2013.01); *C07K 2319/02* (2013.01); *C07K 2319/03* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 4,965,195 A | 10/1990 | Namen et al. | |
| 5,032,396 A | 7/1991 | Williams | |
| 5,229,115 A | 7/1993 | Lynch | |
| 5,231,012 A | 7/1993 | Mosmann et al. | |
| 5,252,714 A | 10/1993 | Harris et al. | |
| 5,328,989 A | 7/1994 | Vellekamp et al. | |
| 5,552,303 A | 9/1996 | Grabstein et al. | |
| 5,624,823 A | 4/1997 | Sachs et al. | |
| 5,643,575 A | 7/1997 | Martinez et al. | |
| 5,665,345 A | 9/1997 | Yarchoan et al. | |
| 5,696,234 A | 12/1997 | Zurawski et al. | |
| 5,705,149 A | 1/1998 | Namen et al. | |
| 5,710,251 A | 1/1998 | Vellekamp et al. | |
| 5,759,859 A | 6/1998 | Leder et al. | |
| 5,824,784 A | 10/1998 | Kinstler et al. | |
| 5,866,134 A | 2/1999 | Fine et al. | |
| 5,876,969 A | 3/1999 | Fleer et al. | |
| 5,908,621 A | 6/1999 | Glue et al. | |
| 5,919,455 A | 7/1999 | Greenwald et al. | |
| 5,932,462 A | 8/1999 | Harris et al. | |
| 5,945,097 A | 8/1999 | Cutler | |
| 5,951,974 A | 9/1999 | Gilbert et al. | |
| 5,985,263 A | 11/1999 | Lee et al. | |
| 5,985,265 A | 11/1999 | Kinstler et al. | |
| 5,985,857 A | 11/1999 | Kinstler et al. | |
| 5,989,867 A | 11/1999 | Knappe et al. | |
| 6,156,301 A | 12/2000 | Namen et al. | |
| 6,217,857 B1 | 4/2001 | Mosmann et al. | |
| 6,387,364 B1 | 5/2002 | Ferguson | |
| 6,428,985 B1 | 8/2002 | Bromberg et al. | |
| 6,660,258 B1 | 12/2003 | Tovey | |
| 6,770,272 B2 | 8/2004 | Strom et al. | |
| 6,989,377 B2 | 1/2006 | Hayes et al. | |
| 7,052,684 B2 | 5/2006 | Ferguson | |
| 7,052,686 B2 | 5/2006 | Lee et al. | |
| 7,056,701 B2 | 6/2006 | Fleer et al. | |
| 7,261,882 B2 | 8/2007 | Watkins | |
| 7,585,947 B2 | 9/2009 | Morre et al. | |
| 7,589,179 B2 | 9/2009 | Gillies et al. | |
| 7,611,700 B2 | 12/2009 | Gantier et al. | |

(Continued)

FOREIGN PATENT DOCUMENTS

| | | |
|---|---|---|
| CN | 1760209 | 10/2004 |
| CN | 102145178 | 8/2011 |

(Continued)

OTHER PUBLICATIONS

Chang et al.—CARs: Synthetic immunoreceptors for cancer therapy and beyond. Trends Mol. Med., 23, 430-450, 2017. (Year: 2017).*
Hermanson et al.—Utilizing chimeric antigen receptors to direct natural killer cell activity. Frontiers in Immunology. 6, 195, 2015. (Year: 2015).*

(Continued)

*Primary Examiner* — Elly-Gerald Stoica
(74) *Attorney, Agent, or Firm* — Robert Brian Johnson

(57) ABSTRACT

Methods of modulating immune responses in subjects having oncology- and immune-related diseases, disorders and conditions by the administration of an IL-10 agent, including pegylated IL-10.

28 Claims, 3 Drawing Sheets

Specification includes a Sequence Listing.

(56) References Cited

U.S. PATENT DOCUMENTS

| | | |
|---|---|---|
| 7,650,243 B2 | 1/2010 | Gantier et al. |
| 7,666,400 B2 | 2/2010 | Chang et al. |
| 7,708,985 B2 | 5/2010 | Morre et al. |
| 7,749,490 B2 | 7/2010 | Sommer et al. |
| 7,939,056 B2 | 5/2011 | Horwitz et al. |
| 8,044,175 B2 | 10/2011 | Dransfield et al. |
| 8,067,532 B2 | 11/2011 | MacLean |
| 8,618,256 B2 | 12/2013 | Cox |
| 8,691,205 B2 | 4/2014 | Blaisdell et al. |
| 8,697,045 B2 | 4/2014 | Lee et al. |
| 8,865,652 B2 | 4/2014 | Lee et al. |
| 9,238,079 B2 | 1/2016 | Lee et al. |
| 9,259,478 B2 | 2/2016 | Blaisdell et al. |
| 9,272,002 B2 | 3/2016 | Powell, Jr. et al. |
| 9,364,517 B2 | 6/2016 | Oft et al. |
| 9,493,740 B2 | 11/2016 | Brenner et al. |
| 2002/0044921 A1 | 4/2002 | Lee et al. |
| 2003/0012775 A1 | 1/2003 | Brandt et al. |
| 2003/0186386 A1 | 10/2003 | Hansen et al. |
| 2004/0213795 A1 | 10/2004 | Collins et al. |
| 2005/0008615 A1 | 1/2005 | Barn et al. |
| 2005/0164352 A1 | 7/2005 | Lauder et al. |
| 2005/0260767 A1 | 11/2005 | Clerici et al. |
| 2006/0046961 A1 | 3/2006 | McKay et al. |
| 2006/0078942 A1 | 4/2006 | Liu et al. |
| 2006/0210534 A1 | 9/2006 | Lee et al. |
| 2006/0258607 A1 | 11/2006 | Jarosch et al. |
| 2007/0134197 A1 | 6/2007 | Eichner et al. |
| 2008/0058246 A1 | 3/2008 | Bhaskaran et al. |
| 2008/0069797 A1 | 3/2008 | Roncarolo et al. |
| 2008/0081031 A1 | 4/2008 | Oft et al. |
| 2008/0096252 A1 | 4/2008 | Zamost et al. |
| 2009/0035256 A1 | 2/2009 | Sommer et al. |
| 2009/0214463 A1 | 8/2009 | Slobedrnan et al. |
| 2009/0214471 A1 | 8/2009 | Oft et al. |
| 2009/0311187 A1 | 12/2009 | Berman et al. |
| 2010/0068147 A1 | 3/2010 | Hibberd et al. |
| 2010/0111898 A1 | 5/2010 | Pelura |
| 2010/0129386 A1 | 5/2010 | Elson et al. |
| 2010/0255496 A1 | 10/2010 | Schrader et al. |
| 2010/0266532 A1 | 10/2010 | Ferguson |
| 2010/0297070 A1 | 11/2010 | Dugan et al. |
| 2011/0009589 A1 | 1/2011 | Harris et al. |
| 2011/0064690 A1 | 3/2011 | Lee et al. |
| 2011/0091419 A1 | 4/2011 | Oft et al. |
| 2011/0250163 A1 | 10/2011 | Blaisdell et al. |
| 2011/0275123 A1 | 11/2011 | Paciotti et al. |
| 2011/0305665 A1 | 12/2011 | Lee et al. |
| 2011/0312010 A1 | 12/2011 | Manuilov |
| 2012/0003221 A1 | 1/2012 | McDonagh et al. |
| 2012/0115926 A1 | 5/2012 | Geary et al. |
| 2012/0142033 A1 | 6/2012 | Fujiwara |
| 2012/0213793 A1 | 8/2012 | Huang et al. |
| 2012/0252742 A1 | 10/2012 | Kranz et al. |
| 2012/0270899 A1 | 10/2012 | Bannister et al. |
| 2012/0321617 A1 | 12/2012 | Osterroth et al. |
| 2013/0156774 A1 | 6/2013 | Kuchroo et al. |
| 2014/0199750 A1 | 7/2014 | Weng et al. |
| 2014/0256626 A1 | 9/2014 | Santi et al. |
| 2014/0314795 A1 | 10/2014 | Riddell et al. |
| 2014/0349402 A1 | 11/2014 | Cooper et al. |
| 2015/0038678 A1 | 2/2015 | Eaton et al. |
| 2015/0118244 A1 | 4/2015 | Shahabi et al. |
| 2016/0340406 A1 | 11/2016 | Zhao et al. |
| 2016/0361415 A1 | 12/2016 | Mumm et al. |
| 2016/0375101 A1 | 12/2016 | Oft |

FOREIGN PATENT DOCUMENTS

| | | |
|---|---|---|
| EP | 0251304 | 1/1988 |
| EP | 2066336 | 9/2012 |
| EP | 2537933 | 12/2012 |
| WO | WO 1992012725 | 8/1992 |
| WO | WO 1992012726 | 8/1992 |
| WO | WO 1994022473 | 3/1994 |
| WO | WO 1994017773 | 8/1994 |
| WO | WO 199503411 | 2/1995 |
| WO | WO 1995003411 | 2/1995 |
| WO | WO 1995006058 | 3/1995 |
| WO | WO 1995019780 | 7/1995 |
| WO | WO 1996011953 | 4/1996 |
| WO | WO 1997003690 | 2/1997 |
| WO | WO 1999032134 | 7/1999 |
| WO | WO 2001005821 | 1/2001 |
| WO | WO 2001058950 | 8/2001 |
| WO | WO 2002026265 | 4/2002 |
| WO | WO 2002085300 | 10/2002 |
| WO | WO 2004044006 | 5/2004 |
| WO | WO 2004056850 | 7/2004 |
| WO | WO 2004091517 | 10/2004 |
| WO | WO 2004106486 | 12/2004 |
| WO | WO 2005033307 | 4/2005 |
| WO | WO 2006075138 | 7/2006 |
| WO | WO 2006094530 | 9/2006 |
| WO | WO 2006119170 | 11/2006 |
| WO | WO 2008054585 | 5/2008 |
| WO | WO 2009016043 | 2/2009 |
| WO | WO 2009036568 | 3/2009 |
| WO | WO 2010022227 | 2/2010 |
| WO | WO 2010077853 | 7/2010 |
| WO | WO 2011051489 | 5/2011 |
| WO | WO 2011159878 | 12/2011 |
| WO | WO 2012004384 | 1/2012 |
| WO | WO 2012050923 | 4/2012 |
| WO | WO 2012050930 | 4/2012 |
| WO | WO 2013113008 | 8/2013 |
| WO | WO 2014172392 | 10/2014 |
| WO | WO 2014176373 | 10/2014 |
| WO | WO 2014204816 | 12/2014 |
| WO | WO 2015031316 | 3/2015 |
| WO | WO 2015070060 | 5/2015 |
| WO | WO 2015108785 | 7/2015 |
| WO | WO 2015153753 | 10/2015 |
| WO | WO 2015187295 | 12/2015 |
| WO | WO 2016064817 | 4/2016 |
| WO | WO 2016106229 | 6/2016 |
| WO | WO 2016126615 | 8/2016 |
| WO | WO 2016145388 | 9/2016 |

OTHER PUBLICATIONS

Jaspers et al.—Development of CAR T cells designed to improve antitumor efficacy and safety. Pharmac. & Therap.—2017—http://dx.doi.org,/10.1016/j.pharmthera.2017.03.012. (Year: 2017).*

Jensen et al.—Designing chimeric antigen receptors to effectively and safely target tumors. Curr. Opin. Immunol. 33, 9-15, 2015. (Year: 2015).*

Chmielewski et al.—TRUCKs: the fourth generation of CARs. Exp. Opin. Biol. Ther., 15, 1145-1154, 2015. (Year: 2015).*

Hombach et al.—OX40 costimulation by a chimeric antigen receptor abrogates CD28 and IL-2 induced IL-10 secretion by redirected CD4+ T cells. OncoImmunol., 1, 458-466, 2012. (Year: 2012).*

Newick et al.—CAR T cell therapy for solid tumors. Annu. Rev. Med. 68, 139-152, 2016. (Year: 2016).*

Gill et al.—Going Viral: chimeric antigen receptor T-cell therapy for hematological malignancies. Immunol. Rev. 263, 68-89, 2015. (Year: 2015).*

Recombinant Mouse I L -1 0 Protein R&D Systems, accessed Feb. 22, 2016.

Berman et al. (1996) "Systemic administration of cellular IL-10 induces an effective, specific, and long-lived immune response against established tumors in mice," *J lmmunol*; 157:231-238.

Chen & Zlotnik (1991) "IL-10: a novel cytotoxic T cell differentiation factor," *J lmmunol*; 147:528-534.

Easy Surf. Blood Volume Calculator [online]Oct. 1, 2012 [retrieved Aug. 18, 2014]. Available on the internet: <URL: https:web.archive.orgweb20121001142649http:www.easysurf.cccnver22.htm >.

Gierens et al. (2000) "Interleukin-6 Stimulates LDL Receptor Gene Expression via Activation of Sterol-Responsive and Sp1 Binding Elements," *Arterioscler Thromb Vasc Biol.*; 20:1777-1783.

(56) References Cited

OTHER PUBLICATIONS

Hombach et al. (2013) "Arming Cytokine-induced Killer Cells With Chimeric Antigen Receptors: CD28 Outperforms Combined CD28-0X40 'Super-stimulation'," *Molecular Therapy*; 12:2268-2277.
Jevševar et al. (2010) "PEGylation of therapeutic proteins," *Biotechnol. J.*; 5:113-128.
Josephson et al. (2001) "Crystal Structure of the IL-10IL-10R1 Complex Reveals a Shared Receptor Binding Site," *Immunity*; 14:35-46.
Khow and Suntrarachun (2012) "Strategies for production of active eukaryotic proteins in bacterial expression system," *Asian Pac. J. Biomed.*; 2(2):159-162.
Kokura et al. (2003) "The blocking of NFkB activation by systemicinterleukin-10 gene therapy inhibits liver and lung metastasis of colon 26 adenocarcinoma in mice" *Gastroenterology*; 124(4): Abstract No. W965.
Maus et al. (2014) "Antibody-modified T cells: CARs take the front seat for hematologic malignancies," *Blood*; 123(17):2625-2635.
Muecke, Susanne, et al., (2000) "Suppression of the Tumorigenic Growth of Burkitt's Lymphoma Cells in Immunddeficient Mice By Cytokine Gene Transfer Using Ebv—Derived Episomal Expression Vectors", Int. J. Cancer, 86:301-306.
Mumm, John B., et al., (2012) "Killing from within" OncoImmunology, 1(9):1598-1600.
Reynolds, et al. (2002) "Proteolytic 180 Labeling for Comparative Proteomics: Evaluation of Endoprotease Glu-C as the Catalytic Agent," *Journal of Proteome Research*; 1(1):27-33.
Zdanov et al. (1996) "Crystal structure of human interleukin-10 at 1.6 A resolution and a model of a complex with its soluble receptor," *Protein Sci.*; (10):1955-1962.
Abbasi, Amanullah, et al., (2012) "Serum Cholesterol: Couid it be a Sixth Parameter of Child-Pugh Scoring System in Cirrhotics Due to Viral Hepatitis?", Journal ofthe College of Physicians and Surgeons Pakistan, 22(8):484-487.
Alpdogan, et al., (2005) "IL-7 and IL-15: therapeutic cytokines for immunodeficiency", Cell, 26(1):56-64.
Anstee and Goldin, (2006) "Mouse models in non-alcoholic fatty liver disease and steatohepatitis research", Int. J. Exp. Path., 87:1-16.
Bieghs, et al., (2012) "LDL Receptor Knock-Out Mice Are a Physiological Model Particularly Vulnerable to Study the Onset of Inflammation in Non-Alcoholic Fatty Liver Disease", PLoS One, 7(1):1-11.
BioLegend, "Recombinant Human IL-10 (carrier-free)", (2007) 3 pages.
Cosma, Meda, (2014) :The impact of cytokines and chemokines on non-alcoholic fatty liver disease (NAFLD), Biotechnology, Molecular Biology and Nanomedicine, 2(1):15-16.
Fry and Mackall (2005) ""The Many Faces of IL-7: From Lymphopoiesis toPeripheral T Cell Maintenance"", the Journal of Immunology, 174:6571-6576.
Gotoh, Koro, (2012) "Spleen-Derived Interleukin-10 Downregulates the Severity of High-Fat Diet-Induced Non-Alcoholic Fatty Pancreas Disease", PLOS, 12 pages.
Gotoh, Koro, et al., (2017) "Role of spleen-derived IL-10 in prevention of systemic low-grade inflammation by obesity", Endocrine Journal, 64(4):375-378.
Larter and Yeh, (2008) "Animal models of NASH: Getting both pathology and metabolic context right", Journal of Gastroenterology and Hepatology, 23:1635-1648.
Lauw, Fanny, et al., (2000) "Proinflammatory Effects of IL-10 During Human Endotoxemia", J Immunol, 165:2783-2789.
Liang, et al., (2014) "Establishment of a General NAFLD Scoring System for Rodent Models and Comparison to Human Liver Pathology", PLOSone, 17 pages.
Liedtke, et al., (2013) "Experimental liver fibrosis research: update on animal models, legal issues and translational aspects", Fibrogenesis Tissue Repair, 6(19):1-25.

Millic, Sandra, et al., (2014) "Non-alcoholic fatty liver disease and obesity: Biochemical, metabolic and clinical presentations", World J Gastroenterol, 20(28):9330-9337.
NCT01025297, (2012) ""Dose Escalation Study of Interleukin7(IL7) and Bitherapy in HCV Genotype 1 or 4 Patients Resistant to Bitherapy Alone (Eclipse 2)"", Clinical Trials, 6 pages.
Nelson, David R., (2003) "Long-Term Interleukin 10 Therapy in Chronic Hepatitis C Patients Has a Proviral and Anti-inflammatory Effect", Hepatology, 38(4):859-868.
Neyrinck, Audrey, et al., (2002) "Inhibition of Kupffer cell activity induces hepatic triglyceride synthesis in fasted rats, independent of lipopolysaccharide challenge", Journal of Hepatology, 36:466-473.
Paulsen and Reichelt, (1992) "Mouse liver regeneration after carbon tetrachloride injury as test system for hepatic growth regulators" Virchows Archiv B Cell Pathol, 62:173-177.
PeproTech, "Recombinant Human IL-10 (carrier-free)", (2017) 7 pages.
Scotton and Chambers, (2010) "Bleomycin revisited: towards a more representative model of IPF?", Am J Physiol Lung Cell Mol Physiol, 299:L439-L441.
Spoto, et al., (2013) "Spleen IL-10, A Key Player in Obesity-Driven Renal Risk", Nephrol Dial Transplant, 28:1061-1064.
Stoklasek, et al., (2006) "Combined IL-15/1L-15Rα Immunotherapy Maximizes IL-15 Activity In Vivo", J Immunol, 177(9):6072-6080.
Storek, et al., (2003) ""Interleukin-7 improves CD4 T-cell reconstitution after autologous CD34 celltransplantation in monkeys"", Blood, 101(10):4209-4218.
Wan, Jinghong, et al., (2014) "M2 Kupffer Cells Promote M1 Kupffer Cell Apoptosis: A Protective Mechanism Against Alcoholic and Nonalcoholic Fatty Liver Disease", Hepatology, 59(1):131-142.
Woodhouse, Stephen D., et al., (2010) "Transcriptome Sequencing, Microarray, and Proteomic Analyses Reveal Cellular and Metabolic Impact of Hepatitis C Virus Infection InVitro", Hepatology, 52(2):443-453.
"Guidance for Industry Immunogenicity Assessment for Therapeutic Protein Products," (2013) *FDA Guidances*.
"Highlights of Prescribing Information," (1997) *Rituxan*.
Accession AAC23839.1; GI 3242896; Jun. 8, 2000.
Accession ABY86619.1; GI 166244598 ; Feb. 4, 2008.
Accession NP_001009327.1; GI 57164347; Feb. 13, 2011.
Accession NP_036986.2; GI 148747382; Aug. 10, 2014.
Accession NP_776513.1; GI 41386772; Jan. 4, 2015.
Agata et al. (1996) "Expression of the PD-1 antigen on the surface of stimulated mouse T and B lymphocytes," *Int Immunol*; 8(5):765-772.
Aggen (2010) "Engineering Human Single-Chain T Cell Receptors," *Dissertation*; http://hdl.handle.net/2142/18585.
Alvarez et al. (2012) "Effects of PEGylation and Immune Complex Formation on the Pharmacokinetics and Biodistribution of Recombinant Interleukin10 in Mice," *Drug Metab Dispos*; 40(2):360-373.
Ansari and Raghava (2010) "Identification of conformational B-cell Epitopes in an antigen from its primary sequence," *Immunome Res*; 6:9pgs.
Ansell et al. (2002) "Phase 1 study of interleukin-12 in combination with rituximab in patients with B-cell non-Hodgkin lymphoma," *Blood*; 99:67-74.
Arakawa and Tsumoto (2003) "The effects of arginine on refolding of aggregated proteins: not facilitate refolding, but suppress aggregation," *Biochemical and Biophysical Research Communications*; 304:148-152.
Armstrong et al. (1996) "Interleukin 10 (IL-10) regulation of tumour necrosis factor cx (TNF-cx) from human alveolar macrophages and peripheral blood monocytes," *Thorax*; 51:143-149.
Asadullah et al. (1999) "Interleukin 10 Treatment of Psoriasis," *Arch Dermatol.*; 135-187-192.
Asadullah et al. (2003) "Interleukin 10 Therapy—Review of a New Approach," *Pharmacol. Rev.*; 55-241-269.
Aukrust et al., (2005) "Potential role for immunomodulatory therapy in atherosclerotic plaque stabilization", Expert Opinion Pharmacother, 6:2169-2180.
Bajetta et al. (1998) "Pilot Study of Subcutaneous Recombinant Human Interleukin 12 in Metastatic Melanoma," *Clinical Cancer Research*; 4:75-85.

(56) References Cited

OTHER PUBLICATIONS

Banerjee et al. (2012) "Poly(ethylene glycol)-Prodrug Conjugates: Concept, Design, and Applications," *Journal of Drug Delivery*; Article ID 103973:17 pages.

Bea at al. (2011) "Performance Evaluation of a Multiplex Assay for Future Use in Biomarker Discovery Efforts to Predict Body Composition," *Clin Chem Lab Med.*; 49(5):817-824.

Berger et al. (2009) "Safety and immunologic effects of IL-15 administration in nonhuman primates," *Blood*; 114:2417-2426.

Berman et al. (1996) "Systemic administration of cellular IL-10 induces an effective, specific, and long-lived immune response against established tumors in mice," *J Immunol*; 157:231-238.

Bilzer et al. (2006) "Role of Kupffer cells in host defense and liver disease," *Liver International*; 26:1175-1186.

Biswas et al. (2007) "Pathogen_specific CD8 T Cell Responses Are Directly Inhibited by IL-10," *J Immunol.*; 179:4520-4528.

Bork, Peer, (2000) "Powers and Pitfalls in Sequence Analysis: The 70% Hurdle", Genome Research, 10:398-400.

Bowie, James, U., et al. (1990) "Deciphering the Message in Protein Sequences: Tolerance to Amino Acid Substitutions", Science, 247:1306-1310.

Brady et al. (1994) "Reflections on a peptide," *Nature*; 368:692-693.

Brooks et al. (2008) "IL-10 and PD-L1 operate through distinct pathways to suppress T-cell activity during persistent viral infection," *PNAS*; 105(51):20428-20433.

Brown, Christine E., et al. (2016) "Regression of Glioblastoma after Chimeric Antigen Receptor T-Cell Therapy", N Engl J Med, 375(26):2561-2569.

Burgess (2009) "Refolding Solubilized Inclusion Body Proteins," *Methods in Enzymology*; 463:259-282.

Burgess, Wilson, H., et al. (1990) "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", J. Cell Biol., 111:2129-2138.

Cai et al. (1999) "IL-10 enhances NK cell proliferation, cytotoxicity and production of IFN-q when combined with IL-18," *Eur. J. Immunol.*; 29:2658-2665.

Caliceti et al. (2012) "Effect of Plasma Membrane Cholesterol Depletion on Glucose Transport Regulation in Leukemia Cells," *PLoS One*; 7:e41246.

Cannistra & Niloff (1996) "Cancer of the uterine cervix," *New Eng I J Med* 334:1030-1038.

Cao et al. (2011) "Janus kinase activation by cytokine oncostatin M decreases PCSK9 expression in liver cells," *J Lipid Res.*; 52(3):513-530.

Capitini et al. (2009) "Modulating T cell Homeostasis with IL-7: Preclinical and Clinical Studies," *J Intern Med*; 266(2):141-153.

Cebon et al. (2003) "Two phase I studies of low dose recombinant human IL-12 with Melan-A and influenza peptides in subjects with advanced malignant melanoma," *Cancer Immunity*; 3:7 (18 pages).

Chamow et al. (1994) "Modification of CD4 Immunoadhesin with Monomethoxypoly(ethylene glycol) Aldehyde via Reductive Alkylation," *Bioconjugate Chem.*; 5:133-140.

Chan et al. (2015) "The Potentiation of IFN-γ and Induction of Cytotoxic Proteins by Pegylated IL-10 in Human CD8 T Cells," *J Interferon Cytokine Res*; 35(12):948-955.

Chen & Zlotnik (1991) "IL-10: a novel cytotoxic T cell differentiation factor," *J Immunol*; 147:528-534.

Chen et al. (2007) "Prediction of linear B-cell epitopes using amino acid pair antigenicity scale," *Amino Acids*; 33:423-428.

Cheon, H.G. (2013) "Latest research and development trends in non insulin anti-diabetics", Arch. Pharm. Res., 36:145-153.

Choi et al. (2006) "Serum adiponectin, interleukin-10 levels and inflammatory markers in the metabolic 1-18 syndrome," *Diabetes Research and Clinical Practice*; 75:235-240.

Cindric, et al., (2007) "Structural 1-16 characterization of PEGylated rHuG-CSF and location of PEG attachment sites". Journal of Pharmaceutical and Biomedical Analysis. New York. NY. US, 44(2):388-395.

Collins et al. (2012) "Trastuzumab induces antibody-dependent cell mediated cytotoxicity (ADCC) in HER-2-non-amplified breast cancer cell lines," *Annals of Oncology*; 23:1788-1795.

Compton et al. (2004) "Pathogenesis of Enterotropic Mouse Hepatitis Virus in Immunocompetent and Immunodeficient Mice," *Comparative Medicine*; 54(6):681-689.

Conlon et al. (2014) "Redistribution, Hyperproliferation, Activation of Natural Killer Cells and CDS T Cells, and Cytokine Production During First-in-Human Clinical Trial of Recombinant Human Interleukin-15 in Patients With Cancer," *Journal of Clinical Oncology*; 33(1):74-82.

Couder et al. (1993) "Synthesis and biological activities of ψ(CH2NH) pseudopeptide analogues of the C-terminal hexapeptide of neurotensin," *Int. J. Peptide Protein Res.*; 41:181-184.

D'Andrea et al. (1993) "Interleukin 10 (IL-10) Inhibits Human Lymphocyte Interferon 3,-Production by Suppressing Natural Killer Cell Stimulatory Factor/IL-12 Synthesis in Accessory Cells," *J. Exp. Med*; 178:1041-1048.

Das et al. (2012) "IL-10—Producing Regulatory B Cells in the Pathogenesis of Chronic Hepatitis B Virus Infection," *J. Immunol.*; 189(8):3925-3935.

Davidson & Diamond (2001) "Autoimmune diseases," *New Engl J Med*; 345:340-350.

De Waal Malefyt et al. (1991) "Interleukin 10 (IL-10) and viral IL-10 strongly reduce antigen-specific human T cell proliferation by diminishing the antigen-presenting capacity of monocytes via downregulation of class II major histocompatibility complex expression," *J Exp Med*; 174(4):915-924.

De Waal Malefyt et al. (1991) "Interleukin 10(IL-10) Inhibits Cytokine Synthesis by Human Monocytes: An Autoregulatory Role of IL-10 Produced by Monocytes," *J. Exp. Med*; 174:1209-1220.

Devay et al. (2013) "Characterization of Proprotein Convertase Subtilisin/Kexin Type 9 (PCSK9) Trafficking Reveals a Novel Lysosomal Targeting Mechanism via Amyloid Precursor-like Protein 2 (APLP2)," *J. Biol. Chem.*; 288:10805-10818.

Dolgin (2011) "Trial puts niacin—and cholesterol dogma—in the line of fire," *Nature Medicine*; 17(7):356.

Dorner et al. (2011) "A genetically humanized mouse model for hepatitis C virus infection," *Nature*; 474:208-211.

Easy Surf. Blood Volume Calculator [online]Oct. 1, 2012 [retrieved Aug. 18, 2014]. Available on the internet: <URL: https://web.archive.org/web/20121001142649/httpi/www.easysurfcc/cnver22.htm >.

Ehrilich et al. (2013) "Preparation and Characterization of Albumin Conjugates of a Truncated Peptide YY Analogue for Half-Life Extension," *Bioconjug. Chem.*; 24(12):2015-2024.

El-Manzalawy et al. (2008) "Predicting linear B-cell epitopes using string kernels," *J Mol Recognit*; 21:243-255.

Emmerich et al. (2012) "IL-10 directly activates and expands tumor-resident CD8(+) T cells without de novo infiltration from secondary lymphoid organs," *Cancer Res*; 72(14):3570-3581.

Engel et al. (2006) "Using Endoproteinases Asp-N and Glu-C to Improve Protein Characterization," *Promega Corporation*; 10th edition.

Enzinger & Mayer (2003) "Esophageal cancer," *New Eng I J Med*; 349:2241-2252.

Fahnert et al. (2012) "Using Folding Promoting Agents in Recombinant Protein Production: A Review," *Methods inn Molecular Biology*; 824:3-36.

Fang et al. (2015) "Programmed Death 1 (PD-1) is involved in the development of proliferative diabetic retinopathy by mediating activation-induced apoptosis," *Mol Vis*; 21:901-910.

Farrar et al. (1999) "Cancer dormancy. VII. A regulatory role for COB+ T cells and IFN-gamma in establishing and maintaining the tumor-dormant state," *J Imunol* 162:2842-2849.

Fehniger and Caligiuri (2001) "Interleukin 15: biology and relevance to human disease," *Blood*; 97:14-32.

Feingold et al. (1996) "Endotoxin, TNF, and IL-I decrease cholesterol 7a-hydroxylase mRNA levels and activity," *Journ of Lipid Res*; 37:223-228.

(56) References Cited

OTHER PUBLICATIONS

Fichtlscherer et al., (2004) "Interleukin-10 serum levels and systemic endothelial vasoreactivity in patients with coronary artery desease", J. Am. Coll. Cardiol., 44:44-49.
Fiorentino et al. (1989) "Two types of mouse T helper cell. IV. Th2 clones secrete a factor that inhibits cytokine production by Th1 clones," *J Exp Med*; 170:2081-2095.
Forastiere et al. (2001) "Head and neck cancer," *New Engl J Med* 345:1890-1900.
Fridman et al. (2012) "The immune contexture in human tumours: impact on clinical outcome," *Nature*; 12:298-306.
Fry and Mackall (2002) "Interleukin-7: from bench to clinic," *Blood*; 99:3892-3904.
Fujiwara et al. (2010) "Extraction and purification of human interleukin-10 from transgenic rice seeds," *Protein Expression and Purification*; 72:125-130.
Gabriel, A., (2007) "Changes in plasma cholesterol in mood disorder patients: Does treatment make a difference?", Journal of Affective Disorders, 99:273-278.
Galon et al. (2013) "The Continuum of Cancer Immunosurveillance: Prognostic, Predictive, and Mechanistic Signatures," *Immunity*; 39:11-26.
Gameren et al. (1994) "Effects of Recombinant human interleukin-6 in cancer patients: a phase I-II study," *Blood*; 84:1434-1441.
Gao et al. (2012) "BEST: Improved Prediction of B-Cell Epitopes from Antigen Sequences," *PLoS One*; 7(6): e40104.
Gargett et al.: 11 Different cytokine and stimulation conditions influence the expansion and immune phenotype of third-generation chimeric antigen receptor T cells specific for tumor antigen GD2, Cytotherapy, vol. 17, No. 4, Apr. 2015 (Apr. 2015) pp. 487-495.
GenBank Accession No. M37897 "Mouse interleukin 10 mRNA, complete cds," dated Apr. 27, 1993.
GenBank Accession No. NP 000563 "interleukin-10 precursor [*Homo sapiens*]," dated Mar. 3, 1995.
Georgescu et al. (1997) "Interleukin-10 Promotes Activation-induced Cell Death of SLE Lymphocytes Mediated by Fas Ligand," *J. Clin. Invest.*; 100:2622-2633.
Gerstein et al. (2008) "Effects of Intensive Glucose Lowering in Type 2 Diabetes," *New England J of Medicine*; 358(24):2545-2559.
Gesser et al. (1997) "Identification of functional domains on human interleukin 10," *Proc. Natl. Acad. Sci.*; 94:14620-14625.
Gierens et al. (2000) "Interleukin-6 Stimulates LDL Receptor Gene Expression via Activation of Sterol-Responsive and Sp1 Binding Elements," *Arterioscier Thromb Vasc Biol.*; 20:1777-1783.
Gill et al., (2015) "Going viral: Chimeric antigen receptor T-cell therapy for hematological malignancies", Immunological Reviews 28150181 Blackwell Publishing Ltd GBR, vol. 263, No. 1, pp. 68-89.
Gregoriadis et al., (2005) "Improving the therapeutic efficacy of peptides and proteins: A role for polysialic acids," *Int. J. Pharmaceutics*; 300(1-2):125-130.
Groux et al. (1998) "A transgenic model to analyze the immunoregulatory role of IL-10 secreted by antigen-presenting cells," *J Immunol*; 162:1723-1729.
Groux et al. (1998) "Inhibitory and stimulatory effects of IL-10 on human COB+ T cells," *J Immunol*; 160:3188-3193.
Hagenbaugh et al. (1997) "Altered immune responses in interleukin 10 transgenic mice," *J Exp Med*; 185:2101-2110.
Hamada et al. (2009) "Effect of Additives on Protein Aggregation," *Current Pharm Biotech*; 10:400-407.
Hashizume et al. (2010) "Overproduced interleukin 6 decreases blood lipid levels via upregulation of very-low-density lipoprotein receptor," Ann Rheum Dis; 69:741-746.
Heeschen et al. (2003) "Serum Level of the Antiinflammatory Cytokine Interleukin-10 Is an Important Prognostic Determinant in Patients With Acute Coronary Syndromes," *Circulation*; 107:2109-2114.
Hombach et al. (2013) "Arming Cytokine-induced Killer Cells With Chimeric Antigen Receptors: CD28 Outperforms Combined CD28-OX40 'Super-stimulation'," *Molecular Therapy*; 12:2268-2277.
Howard et al. (1993) "Interleukin 10 Protects Mice from Lethal Endotoxemia," *J. Exp. Med.*; 177:1205-1208.
Huang et al. (1996) "Interleukin 10 Suppresses Tumor Growth and Metastasis of Human Melanoma Cells: Potential Inhibition of Angiogenesis," Clinical Cancer Research, *The American Assn for Cancer Research*; 2(12):1969-1979.
Huang et al. (2010) "Depletion of Liver Kupffer Cells Prevents the Development of Diet-Induced Hepatic Steatosis and Insulin Resistance," 59:347-357.
Huntington et al. (2008) "IL-15 trans-presentation promotes human NK cell development and differentiation in vivo," *J. Exp. Med.*; 206:25-34.
Hustoft et al. (2012) "A Critical Review of Trypsin Digestion for LC-MS Based Proteomics," *InTech*; Chapter 4.
Infante et al. (2015) "A first-in-human dose escalation study of PEGylated recombinant human IL-10 (AM0010) in advanced solid tumors," *ASCO Meeting Abstracts*; 33(15 suppl):3017.
International Search Report; PCT/US01/42431, dated Aug. 20, 2002.
Ishikawa et al. (2005) "Interleukin-10 plasmid DNA inhibits liver and lung metastasis of Colon 26 adenocarcinoma in mice," *Proceedings of the Annual Meeting, American Association for Cancer Research*; vol. 46, Abstract # 3364.
Izbicki et al. (1997) "Prognostic value of immunohistochemically identifiable tumor cells in lymph nodes of patients with completely resected esophageal cancer," *New Engl J Med*; 337:1188-1194.
Jameson et al. (1994) "A rationally designed CD4 analogue inhibits experimental allergic encephalomyelitis," *Nature*; 368:744-746.
Jevšvar et al. (2010) "PEGylation of therapeutic proteins," *Biotechnol. J.*; 5:113-128.
Jiang et al. (2015) "T-cell exhaustion in the tumor microenvironment," *Cell Death Dis*; 6:e1792.
Josephson et al. (2001) "Crystal Structure of the IL-10/IL-10R1 Complex Reveals a Shared Receptor Binding Site," *Immunity*; 14:35-46.8
Jungbauer et al. (2007) "Current status of Technical protein refolding," *Journal of Biotechnology*; 128:587-596.
Katre (1993) "The Conjugation of Proteins with Polyethylene Glycol and Other Polymers Altering Properties of Proteins to Enhance their Therapeutic Potential," *Advanced Drug Delivery Reviews*; 10(1):91-114.
Know and Suntrarachun (2012) "Strategies for production of active eukaryotic proteins in bacterial expression system," *Asian Pac. J. Biomed.*; 2(2):159-162.
Kimball et al (2002) "Clinical and Immunologic Assessment of Patients With Psoriasis in a Randomized, Double-blind, Placebo-Controlled Trial Using Recombinant Human Interleukin 10," *Arch Dermatol*; 138:1341-1346.
Kinstler et al. (1996) "Characterization and Stability of N-terminally PEGylated rhG-CSF," *Pharm. Res.*; 13:996-1002.
Kinstler et al. (2002) "Mono-N-terminal poly(ethylene glycol)—protein conjugates," *Advanced Drug Delivery Reviews*; 54:477-485.
Klebanoff, CA et al., (2004) "IL-15 Enhances the in vivo Antitumor Activity of Tumor-reactive CD8+ T Cells", Proceedings of the National Academy of the Sciences of the U.S.A., 101(7):1969-1974.
Klompus et al. (2008) "A simple novel method for the preparation of noncovalent homodimeric, biologically active human interleukin 10 in *Escherichia coli*—Enhancing protein expression by degenerate PCR of 59 DNA in the open reading frame," *Protein Expression and Purification*; 62:199-205.
Kokura et al. (2003) "The blocking of NFkB activation by systernicinterleukin-10 gene therapy inhibits liver and lung metastasis of colon 26 adenocarcinoma in mice" *Gastroenterology*; 124(4): Abstract No. W965.
Kokura et al. (2005) "Interleukin-1 0 plasmid DNA inhibits subcutaneous tumor growth of Colon adenocarcinoma in mice," *Cancer Letters*; 218:171-179.
Kong et al. (2005) "In vivo activities of cytokine oncostatin M in the regulation of plasma lipid levels," *Journal of Lipid Research*; 46:1163-1171.
Körholz et al. (1997) "The Role of Interleukin-10 (IL-10) in IL-15—Mediated T-Cell Responses," *Blood*; 90(11):4513-4521.

(56) References Cited

OTHER PUBLICATIONS

Kundu et al. (1996) "Antimetastatic and antitumor activities of interleukin 10 in a murine model of breast cancer," *J Nail Cancer Inst*; 88:536-541.
Kundu et al. (1997) "Interleukin-10 inhibits tumor metastasis, down regulates MHC class I, enhances NK lysis," *Cellular Immunology, Academic Press*; 180(1):55-61.
Kute et al. (2012) "Understanding key assay parameters that affect measurements of trastuzumab-mediated ADCC against Her2 positive breast cancer cells," *OncoImmunology*; 1(6):810-821.
Langowski et al. (2006) "IL-23 promotes tumour incidence and growth," *Nature*; 442:461-465.
Lasek et al. (2014) "Interleukin 12: still a promising candidate for tumor immunotherapy?" *Cancer Immunol Immunother*; 63:419-435.
Lazar, Eliane, et al. (1988) "Transforming Growth Factor alpha: Mutation of Aspartic Acid 47 and Leucine 48 Results in Different Biological Activities", Mol. Cell. Bioi., 8:1247-1252.
Le et al. (2001) "Pre-existing tumor-sensitized T cells are essential for eradication of established tumors by IL-12 and cyclophosphamide plus IL-12," *J Immunol*; 167:6765-6772.
Lehmann et al. (2014) "IL-12 Directs Further Maturation of Ex Vivo Differentiated NK Cells with Improved Therapeutic Potential," *PLoS One*; 9(1):e87131 (12 pages).
Lewington and Clark (2005) "Combined Effects of Systolic Blood Pressure and Total Cholesterol on Cardiovascular Disease Risk," *Circulation*; 112:3373-3374.
Lindhout et al. (2011) "Site-specific enzymatic polysialylation of therapeutic proteins using bacterial enzymes," *PNAS*; 108(18)7397-7402.
Liu et al. (2003) "IL-10 Mediates Suppression of the CD8 T Cell IFN-γ Response to a Novel Viral Epitope in a Primed Host," *J Immunol*; 171:4765-4772.
Loebbermann et al. (2012) "IL-10 Regulates Viral Lung Immunopathology during Acute Respiratory Syncytial Virus Infection in Mice," *PLoS One*; 7(2):e32371.
Lopez et al. (2005) "IL-12 and IL-10 Expression Synergize to Induce the Immune-Mediated Eradication of Established Colon and Mammary Tumors and Lung Metastasis," *J Immunol*; 175:5885-5894.
Lowe et al. (1998) "Impact of Major Cardiovascular Disease Risk Factors, Particularly in Combination, on 22-Year Mortality in Women and Men," *Arch Intern Med*; 158:2007-2014.
Lu et al. (2004) "Prognostic factors in resected stage I non-small-cell lung cancer: a multivariate analysis of six molecular markers," *J Clin Oneal*; 22:4575-4583.
Lugli et al. (2010) "Transient and persistent effects of IL-15 on lymphocyte homeostasis in nonhuman primates," *Blood*; 116:3238-3248.
Lynch and Chapelle (2003) "Hereditary colorectal cancer," *New Eng I J Med*; 348:919-932.
Martin et al. (2001) "B-Cell Deficiency Suppresses Vaccine-Induced Protection against Murine Filariasis but Does Not Increase the Recovery Rate for Primary Infection," *Infect. Immun.*; 69(11):7067-7073.
Mattos et al. (2012) "PEGylation of interleukin-10 improves the pharmacokinetic profile and enhances the antifibrotic effectivity in CCl.-induced fibrogenesis in mice," *J Control Release*; 162(1):84-91.
Maus et al. (2014) "Antibody-modified T cells: CARs take the front seat or hematologic malignancies," *Blood*; 123(17):2625-2635.
Miki Toyokazu et al. (2000) "Anti-metastatic effect of IL-10 gene modification in human lung cancer cells is differentially regulated by organ microenvironments," *Proceedings of the Annual Meeting American Association for Cancer Research*; 41:3.
Monk (2011) "A Strategy for the Quantification of Protein Polyethylene Glycol (PEG) Derivatized Sites using iTRAQ," *University of California*, San Diego; 1-51.

Moore et al. (1990) "Homology of cytokine synthesis inhibitory factor (IL-10) to the Epstein-Barr virus gene BCRFI," *Science*; 248:1230-1234.
Moran et al. (1994) "Human leukemia inhibitory factor inhibits development of experimental atherosclerosis," *Arterioscler Thromb Vasc Biol.*; 14(8):1356-1363.
Motzer et al. (2001) "Randomized Multicenter Phase II Trial of Subcutaneous Recombinant Human Interleukin-12 Versus Interferon-α2a for Patients with Advanced Renal Cell Carcinoma," *Journal of Interferon and Cytokine Research*; 21:257-263.
Muecke, Susanne, et al., (2000) "Suppression of the Tumorigenic Growth of Burkitt's Lymphoma Cells in Immunodeficient Mice by Cytokine Gene Transfer Using Ebv-Derived Episomal Expression Vectors", Int. J. Cancer, 86:301-306.
Mumm et al. (2011) "IL-10 elicits IFNγ-dependent tumor immune surveillance," *Cancer Cell*; 20(6):781-796.
Mumm et al., (2012) "Killing from within" OncoImmunology, 1(9)1 598-1600.
Naicker et al. (2009) "Interleukin-10 Promoter Polymorphisms Influence HIV-1 Susceptibility and Primary HIV-1 Pathogenesis," *J. Infect. Dis.*; 200(3):448-452.
Natsume et al. (2009) "Improving effector functions of antibodies for cancer treatment: Enhancing ADCC and CDC," *Drug Design, Development and Therapy*; 3:7-16.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors". ClinicalTrials.gov, Dec. 11, 2013, 3 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors". ClinicalTrials.gov, Jan. 31, 2014, 3 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jul. 17, 2014, 6 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Mar. 24, 2015, 7 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jan. 12, 2016, 7 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors". ClinicalTrials.gov, Oct. 2, 2016, 7 pages.
NCT02923921, "Randomized Study of AM0010 in Combination With FOLFOX Compared to FOLFOX Alone as Secondline Tx in Pts With Meta Pancreatic Cancer That Has Progressed During or Following a FirstLine Gemcitabine Containing Regimen", ClinicalTrials. gov, Oct. 4, 2016, 3 pages.
Nenseter et al. (1992) "Role of liver endothelial and Kupffer cells in clearing low density lipoprotein from blood in hypercholesterolemic rabbits," *J of Lipid Res*; 33:867-877.
Neven et al. (2013) "A Mendelian predisposition to B cell lymphoma caused by IL-10R deficiency," *Blood*; 122(23):3712-3722.
Neyrinck et al. (2009) "Critical role of Kupffer cells in the management of diet-induced diabetes and obesity," *Biochemical and Biophysical Research Communications*; 385:351-356.
Nicholls et al. (2012) "Is niacin ineffective? or did AIM-HIGH miss its target?," *Cleveland Clinic Journ of Med*; 79(1):38-43.
Noguchi et al. (2003) "PDX-1 Protein Containing Its Own Antennapedia-Like Protein Transduction Domain Can Transduce Pancreatic Duct and Islet Cells," *Diabetes*; 52(7):1732-1737.

(56) References Cited

OTHER PUBLICATIONS

O'Rourke, Donald M., et al., (2017) "A single dose of peripherally infused EGFRvIII-directed CAR T cells mediates antigen loss and induces adaptive resistance in patients with recurrent glioblastoma", Science Translational Medicine, 9(399):1 page.
Osaki et al. (1999) "Potent antitumor effects mediated by local expression of the mature form of the interferon-γ inducing factor, interleukin-18 (IL-18)," *Gene Therapy*; 6:808-815.
Osborne (1998) "Tamoxifen in the treatment of breast cancer," *New Engl J Med*; 339:1609-1618.
Overdijk et al. (2011) "Epidermal Growth Factor Receptor (EGFR) Antibody-Induced Antibody-Dependent Cellular Cytotoxicity Plays a Prominent Role in Inhibiting Tumorigenesis, Even of Tumor Cells Insensitive to EGFR Signaling Inhibition," *Journal of Immunology*; 187:3383-3390.
Papadopoulou, Athanassia, et al., (2013) "Plasma total cholesterol in psychiatric patients after a suicide attempt and in follow-up", Journal of Affective Disorders, 148:440-443.
Pardoll (2012) "The blockade of immune checkpoints in cancer immunotherapy," *Cancer*; 12:252-264.
Park et al. (2011) "IL-15-Induced IL-10 Increases the Cytolytic Activity of Human Natural Killer Cells," *Mol. Cells*; 32:265-272.
Pasut and Veronese (2012) "State of the art in PEGylation: The great versatility achieved after forty years of research," *Journal of Controlled Release*; 161:461-472.
Payne et al. (2010) "Product development issues for PEGylated proteins," *Pharmaceutical Development and Technology*; 16:423-440.
Pegram et al. (2012) "Interleukin 12: Stumbling Blocks and Stepping Stones to Effective Anti-Tumor Therapy," *Advancements in Tumor Immunotherapy and Cancer Vaccines*; Chapter 10:197-218.
Pellegrini et al. (2011) "IL-7 Engages Multiple Mechanisms to Overcome Chronic Viral Infection and Limit Organ Pathology," *Cell*; 144:1-13.
Pettit et al. (1997) "Structure-Function Studies of Interleukin 15 using Site-specific Mutagenesis, Polyethylene Glycol Conjugation, and Homology Modeling," *J. Biol. Chem*. 272:2312-2318.
Pjrek, Edda, et al., (2007) "Serum lipid levels in seasonal affective disorder", Eur Arch Psychiatry Clin Neurosci, 257:197-202.
Rachmawati et al. (2004) "Pharmacokinetic and Biodistribution Profile of Recombinant Human Interleukin-10 Following Intravenous Administration in Rats with Extensive Liver Fibrosis," *Pharm. Res.*; 21(11):2072-2078.
Rachmawati et al. (2007) "Chemical Modification of Interleukin-10 with Mannose 6-Phosphate Groups Yields a Liver-Selective Cytokine," *Drug Metabolism and Disposition*; 35(5):814-821.
Radwanski et al. (1998) "Pharmacokinetics and Leukocyte Responses of Recombinant Human Interleukin-10," *Pharm. Res.*; 15(12):1895-1901.
Ramirez-Montagut et al. (2003) "Immunity to melanoma: unraveling the relation of tumor immunity and autoimmunity," *Oncogene*; 22:3180-3187.
Re et al. (2002) "Preclinical evaluation of the antiproliferative potential of STI571 in Hodgkin's disease," *British Journal of Cancer*; 86:1333-1335.
Recombinant Human IL-1 0 Protein, CF R&D Systems, accessed Feb. 22, 2016.
Reynolds, et al. (2002) "Proteolytic 18O Labeling for Comparative Proteomics: Evaluation of Endoprotease Glu-C as the Catalytic Agent," *Journal of Proteome Research*; 1(1):27-33.
Roberts et al. (2012) "Chemistry for peptide and protein PEGylation," *Advanced Drug Delivery Reviews*; 64:116-127.
Rolfe et al. (2003) "Leukemia inhibitory factor retards the progression of atherosclerosis," *Cardiovascular Research*; 58:222-230.
Russo et al. (2006) "Randomized trial of pegylated interferon a-2b monotherapy in haemodialysis patients with chronic hepatitis C," *Nephrol Dial Transplant*; 21:437-443.
Saha and Raghava (2006) "Prediction of continuous B-cell epitopes in an antigen using recurrent neural network," *Proteins*; 65:40-48.

Sakamoto et al. (2003) "Interleukin-10 gene therapy enhances antitumor effect of CPT-11 for lung metastasis of colon26 adenocarcinoma in mice," *Gastroenterology*; 124(4):A456-A457.
Sawaya et al. (2003) "Risk of cervical cancer associated with extending the interval between cervical-cancer screenings," *New Engl J Med*; 349:1501-1509.
Schäffner et al. (2001) "Cosecretion of Chaperones and Low-Molecular-Size Medium Additives Increases the Yield of Recombinant Disulfide-Bridged Proteins," *Applied and Environmental Microbiology*; 67(9):3994-4000.
Schneiderheinze, J., et al., (2009) "Rapid online proteolytic mapping of PEGylated rhGH for identity confirmation. quantitation of methionine oxidation and quantitation of UnPEGylated N-terminus using HPLC with UV detection", Journal of Chromatography B: Biomedical Sciences & Applications. Elsevier. Amsterdam. NL., 877(31):4065-4070.
Sela and Zisman (1997) "Different roles of D-amino acids in immune phenomena," *Faseb J.*; 11:449-456.
Shen et al. (2013) "Proprotein convertase subtilisin/kexin type 9 potentially influences cholesterol uptake in macrophages and reverse cholesterol transport," *FEBS Letters*; 587:1271-1274.
Smith et al. (1996) "Administration of interleukin-1 0 at the time of priming protects Corynebacterium parvum-primed mice against LPS- and TNF-alpha-induced lethality," *Cellular Immunology* 173(2):207-214.
Sneller et al. (2011) "IL-15 administered by continuous infusion to rhesus macaques induces massive expansion of CD8 T effector memory population in peripheral blood," *Blood*; 118(26):6845-6848.
Soderquist, et al. (2010) "PEGylation of interleukin-1 0 for the mitigation of enhanced pain states", J Biomed Mater Res A, 3(93):1169-1179.
Soman et al. (2009) "MTS dye based colorimetric CTLL-2 cell proliferation assay for product release and stability monitoring of Interleukin-15: Assay qualification, standardization and statistical analysis," *J Immunol Methods*; 348(1-2):83-94.
Song et al. (2012) "CD27 costimulation augments the survival and antitumor activity of redirected human T cells in vivo," *Blood*; 119(3):696-706.
Srivastava et al. (2013) "Effects of interleukin-18 on natural killer cells: costimulation of activation through Fc receptors for immunoglobulin," *Cancer Immunol Immunother*; 62(6):1073-1082.
Steel, JC et al., (2012) "Biology and its Therapeutic Implications in Cancer", Trends in Pharmacological Sciences, 33(1):35-41.
Storici and Resnick (2006) "The delitto perfetto approach to in vivo site-directed mutagenesis and chromosome rearrangements with synthetic oligonucleotides in yeast," *Methods in Enzymology*; 409:329-345.
Sweredoski and Baldi (2009) "COBEpro: a novel system for predicting continuous B-cell epitopes," *Protein Eng Des Sel*; 22:113-120.
Syto et al. (1998) "Structural and biological stability of the human interleukin 10 homodimer," *Biochemistry*; 37(48):16943-16951.
Teng et al. (2015) "IL-12 and IL-23 cytokines: from discovery to targeted therapies for immune-mediated inflammatory diseases," *Nature Medicine*; 21:719-729.
Teng et al.: "Stable IL-10: A new therapeutic that promotes tumor immunity" Cancer Cell 2011 Cell Press USA, vol. 20, No. 6 , Dec. 13, 2011 (Dec. 13, 2011) , pp. 691-693.
Tilg et al. (2002) "Treatment of Crohn's disease with recombinant human interleukin 10 induces the proinflammatory cytokine interferon γ," *Gut*; 50:191-195.
Trandem et al. (2011) "Virally Expressed Interleukin-10 Ameliorates Acute Encephalomyelitis and Chronic Demyelination in Coronavirus-Infected Mice," *J. Virol.*; 85(14):6822-6831.
Tréhin et al. (2004) "Cellular uptake but low permeation of human calcitonin-derived cell penetrating peptides and Tat(47-57) through well-differentiated epithelial models," *Pharm. Research*; 21:1248-1256.
Tsumoto et al. (2003) "Practical considerations in refolding proteins from inclusion bodies," *Protein Expression and Purification*; 28:1-8.

(56) References Cited

OTHER PUBLICATIONS

Tsumoto et al. (2004) "Role of Arginine in Protein Refolding, Solubilization, and Purification," *Biotechnol. Prog.*; 20:1301-1308.

UniProt reference A2T6Z6 (IL 1 O_PANTR) (downloaded from http://www.uniprotorg/uniprot!A2T6Z6, last sequence update Mar. 6, 2007).

UniProt reference P79338 (IL 1 O_MACFA) (downloaded from http://www.uniprot.org/uniprot/P79338, last sequence update May 1, 1997).

Valabrega et al. (2007) "Trastuzumab: mechanism of action, resistance and future perspectives in HER2-overexpressing breast cancer," *Annals of Oncology*; 18:977-984.

Van Deventer et al. (1997) "Multiple Doses of Intravenous Interleukin 10 in Steroid-Refractory Crohn's Disease," *Gastroenterology*, 113:383-389.

Vicari and Trinchieri (2004) "Interleukin-10 in viral diseases and cancer: exiting the labyrinth?," *Immunological Reviews*; 202:223-236.

Vigneron et al. (2013) "Database of T cell-defined human tumor antigens: the 2013 update," *Cancer Immunity*; 13:15-20.

Virgin, et al. (2009) "Redefining Chronic Viral Infection," *Cell*; 138:30-50.

Virkkunen, M., (1979) "Serum Cholesterolin Antisocial Personality", Neuropsychobiology, 5:27-30.

Von Andrian and Mackay (2000) "T-cell function and migration. Two sides of the same coin," *New Engl J Med*; 343:1020-1034.

Waldmann et al. (2011) "Safety (toxicity), pharmacokinetics, immunogenicity, and impact on elements of the normal immune system of recombinant human IL-15 in rhesus macaques," *Blood*; 117:4787-4795.

Walter and Nagabhushan (1995) "Crystal structure of interleukin 10 reveals an interferon gamma-like fold," *Biochemistry*; (38):12118-12125.

Wee et al. (2010) "SVM-based prediction of linear B-cell epitopes using Bayes Feature Extraction," *BMC Genomics*; 11(Supp 4):S21.

Wender et al. (2000) "The design, synthesis, and evaluation of molecules that enable or enhance cellular uptake: peptoid molecular transporters," *Proc. Natl. Acad. Sci. USA*; 97:13003-13008.

Wilson et al. (2011) "The role of IL-10 in regulating immunity to persistent viral infections," *Curr Top Microbiol Immunol.*; 350:39-65.

Witsch et al. (2010) "Roles for Growth Facotes in Cancer Progression," *Physiology*; 25(2):85-101.

Wu et al. (2012) "Immunotherapies: The Blockade of Inhibitory Signals," Int. J. Biol. Sci.; 8:1420-1430.

Xu et al. (2010) "Regulation of Antitumor Immune Responses by the IL-12 Family Cytokines, IL-12, IL-23, and IL-27," *Clinical and Developmental Immunology*; Article ID:832454 (9 pages).

Yamaguchi and Miyazaki (2014) "Refolding Techniques for Recovering Biologically Active Recombinant Proteins from Inclusion Bodies," *Biomolecules*; 4:235-251.

Yoshioka et al. (2011) "Development of a novel DDS for site-specific PEGylated proteins," *Chem. Central J.*; 5:25.

Younes et al. (2004) "Phase II Clinical Trial of Interleukin-12 in Patients with Relapsed and Refractory Non-Hodgkin's Lymphoma and Hodgkin's Disease," *Clinical Cancer Research*; 10:5432-5438.

Zauner et al. (1996) "Glycerol Enhancement of Ligand-Polylysine/DNA Transfection," *BioTechniques*; 20:905-913.

Zdanov et al. (1995) "Crystal structure of interleukin-10 reveals the functional dimer with an unexpected topological similarity to interferon $\gamma$," *Structure*; 3:591-601.

Zender et al. (2002) "VP22-mediated intercellular transport of p53 in hepatoma cells in vitro and in vivo," *Cancer Gene Ther.*; 9(6):489-496.

Zheng et al. (1996) "Interleukin-10 inhibits tumor metastasis through an NK cell-dependent mechanism," *J Exp Med*; 184:579-584.

Tilg, et al., "Induction of circulating interleukin 10 by interleukin 1 and interleukin 2, but not interleukin 6 immunotherapy," *Cytokine*, vol. 7, No. 7, pp. 734-739 (1995).

Naing, et al, "Safety, Antitumor Activity, and Immune Activation of Pegylated Recombinant Human Interleukin-10 (AM0010) in Patients with Advanced Solid Tumors," *Journal of Clinical Oncology*, vol. 34, No. 29, pp. 3562-3569 (2016).

\* cited by examiner

METHOD OF MODULATING A CHIMERIC ANTIGEN RECEPTOR T CELL IMMUNE RESPONSE BY ADMINISTERING IL-10

CROSS-REFERENCE TO RELATED APPLICATION

The present application claims priority benefit of U.S. provisional application Ser. No. 62/167,699, filed May 28, 2015, which application is incorporated herein by reference in its entirety.

FIELD OF THE INVENTION

This invention relates to methods of using IL-10 agents to modulate immune responses in the treatment or prevention of oncology- and immune-related diseases, disorders and conditions.

INTRODUCTION

The cytokine interleukin-10 (IL-10) is a pleiotropic cytokine that regulates multiple immune responses through actions on T cells, B cells, macrophages, and antigen presenting cells (APC). IL-10 can suppress immune responses by inhibiting expression of IL-1α, IL-1β, IL-6, IL-8, TNF-α, GM-CSF and G-CSF in activated monocytes and activated macrophages, and it also suppresses IFN-γ production by NK cells. Although IL-10 is predominantly expressed in macrophages, expression has also been detected in activated T cells, B cells, mast cells, and monocytes. In addition to suppressing immune responses, IL-10 exhibits immunostimulatory properties, including stimulating the proliferation of IL-2- and IL-4-treated thymocytes, enhancing the viability of B cells, and stimulating the expression of MHC class II.

Human IL-10 is a homodimer that becomes biologically inactive upon disruption of the non-covalent interactions between the two monomer subunits. Data obtained from the published crystal structure of IL-10 indicates that the functional dimer exhibits certain similarities to IFN-γ (Zdanov et al, (1995) Structure (Lond) 3:591-601).

As a result of its pleiotropic activity, IL-10 has been linked to a broad range of diseases, disorders and conditions, including inflammatory conditions, immune-related disorders, fibrotic disorders, metabolic disorders and cancer. Clinical and pre-clinical evaluations with IL-10 for a number of such diseases, disorders and conditions have solidified its therapeutic potential. Moreover, pegylated IL-10 has been shown to be more efficacious than non-pegylated IL-10 in certain therapeutic settings.

SUMMARY

The present disclosure contemplates the use of an IL-10 agent (e.g., pegylated IL-10) as a component of chimeric antigen receptor-T cell therapy (CAR-T cell therapy). CARs represent an emerging therapy for cancer (e.g., treatment of B and T cell lymphomas) and other malignancies. CAR-T T cells generally comprise patient-derived memory CD8+ T cells modified to express a recombinant T cell receptor specific for a known antigen present on, for example, a tumor of interest. While the present disclosure is generally described in the context of using CAR-T cell therapy for the treatment of cancer, it is to be understood that such therapy is not so limited.

CAR-T T cell therapy comprises use of adoptive cell transfer (ACT), a process which utilizes a patient's own cultured T cells. In CAR-T cell therapy, T cells are removed from a patient and genetically altered to express CARs directed towards antigens specific for a known cancer (e.g., a tumor). Following amplification ex vivo to a sufficient number, the autologous cells are infused back into the patient, resulting in the antigen-specific destruction of the cancer. In this manner, CAR-T T cell therapy is similar to apheresis in which blood taken from a patient is treated in a manner that separates out one particular constituent (e.g., removal of malignant white blood cells in the process of leukocytapheresis) and then the remainder is returned to the patient's circulation.

As discussed further hereafter, treatment with CAR-T cell therapy has, in part, been limited by both the induction of antigen-specific toxicities targeting normal tissues expressing the target-antigen, and the extreme potency of CAR-T cell treatments resulting in life-threatening cytokine-release syndromes. In particular, it has been observed that high affinity T cell receptor interactions with significant antigen burden can lead to activation-induced cell death. Historically, the scientific literature has discussed IL-10 in the context of enhancement of activation-induced cell death (Georgescu et al. (1997) J Clin Invest 100(10):2622-33). However, the data presented herein suggest that an IL-10 agent may be used in conjunction with CAR-T T cell therapy to prevent or limit activation-induced cell death while enhancing CD8+ T cell function and survival.

As discussed further hereafter, human IL-10 is a homodimer, and each monomer comprises 178 amino acids, the first 18 of which comprise a signal peptide. Particular embodiments of the present disclosure comprise mature human IL-10 polypeptides lacking the signal peptide (see, e.g., U.S. Pat. No. 6,217,857), or mature human PEG-IL-10. In further particular embodiments, the IL-10 agent is a variant of mature human IL-10. The variant can exhibit activity less than, comparable to, or greater than the activity of mature human IL-10; in certain embodiments the activity is comparable to or greater than the activity of mature human IL-10.

Certain embodiments of the present disclosure contemplate modification of IL-10 in order to enhance one or more properties (e.g., pharmacokinetic parameters, efficacy, etc.). Such IL-10 modifications include pegylation, glycosylation, albumin (e.g., human serum albumin (HSA)) conjugation and fusion, and hesylation. In particular embodiments, IL-10 is pegylated. In further embodiments, modification of IL-10 does not result in a therapeutically relevant, detrimental effect on immunogenicity, and in still further embodiments modified IL-10 is less immunogenic than unmodified IL-10. The terms "IL-10", "IL-10 polypeptide(s)," "agent(s)" and the like are intended to be construed broadly and include, for example, human and non-human IL-10-related polypeptides, including homologs, variants (including muteins), and fragments thereof, as well as IL-10 polypeptides having, for example, a leader sequence (e.g., the signal peptide), and modified versions of the foregoing. In further particular embodiments, the terms "IL-10", "IL-10 polypeptide(s), "agent(s)" are agonists. Particular embodiments relate to pegylated IL-10, which is also referred to herein as "PEG-IL-10". The present disclosure also contemplates nucleic acid molecules encoding the foregoing, vectors and the like containing the nucleic acid molecules, and cells (e.g., transformed cells and host cells) that express the IL-10 agents.

The present disclosure contemplates methods of using CAR-T cell therapy and an IL-10 agent to modulate a T cell-mediated immune response to a target cell population in a subject. A particular embodiment contemplates a method of modulating a T cell-mediated immune response to a target cell population in a subject, comprising a) introducing to the subject a therapeutically effective plurality of cells genetically modified to express a chimeric antigen receptor, wherein the chimeric antigen receptor comprises at least one antigen-specific targeting region capable of binding to the target cell population, and wherein the binding of the chimeric antigen receptor targeting region to the target cell population is capable of eliciting activation-induced cell death; and b) administering to the subject a therapeutically effective amount of an IL-10 agent sufficient to prevent or limit the activation-induced cell death. In particular embodiments, the CAR comprises an antigen binding domain which specifically recognizes the target cell population.

In certain embodiments of the present disclosure, the IL-10 agent enhances the function of activated memory CD8+ T cells. In other embodiments, the amount of the IL-10 agent administered is sufficient to enhance cytotoxic function.

Embodiments are contemplated wherein administration of the IL-10 agent is prior to, simultaneously with, or subsequent to administration of the therapeutically effective plurality of cells. In certain embodiments of the present disclosure, the IL-10 agent is administered subcutaneously.

In certain embodiments, the present disclosure contemplates the administration of the IL-10 agent in an amount sufficient to achieve a serum concentration of from 10 to 100 ng/mL. In some embodiments, the IL-10 agent is administered to a subject in an amount sufficient to maintain a mean IL-10 serum trough concentration of from 1 pg/mL to 10.0 ng/mL. In some embodiments, the mean IL-10 serum trough concentration of from 1.0 pg/mL to 10.0 ng/mL is maintained for at least 95% of a defined period of time. In further embodiments of the present disclosure, the mean IL-10 serum trough concentration is in the range of from 1.0 pg/mL to 100 pg/mL; from 0.1 ng/mL to 1.0 ng/mL; from 1.0 ng/mL to 10 ng/mL; from 0.5 ng/mL to 5.0 ng/mL; from 0.75 ng/mL to 1.25 ng/mL or from 0.9 ng/mL to 1.1 ng/mL. In particular embodiments of the present disclosure, the mean IL-10 serum trough concentration is at least 1.25 ng/mL, at least 1.5 ng/mL, at least 1.6 ng/mL, at least 1.7 ng/mL, at least 1.8 ng/mL, at least 1.85 ng/mL, at least 1.9 ng/mL, at least 1.95 ng/mL, at least 1.97 ng/mL, and least 1.98 ng/mL, at least 1.99 ng/mL, at least 2.0 ng/mL or greater than 2 ng/mL.

In further embodiments, the aforementioned period of time is at least 12 hours, at least 24 hours, at least 48 hours, at least 72 hours, at least 1 week, at least 2 weeks, at least 3 weeks, at least 1 month, at least 6 weeks, at least 2 months, at least 3 months, at least 6 months, at least 9 months, or greater than 12 months.

In particular embodiments of the present disclosure, the mean IL-10 serum trough concentration is maintained for at least 85% of the period of time, at least 90%, at least 96%, at least 98%, at least 99% or 100% of the period of time.

It is envisaged that a dosing regimen sufficient to maintain a desired steady state serum trough concentration (e.g., 1 ng/mL) can result in an initial serum trough concentration that is higher than the desired steady state serum trough concentration. Because of the pharmacodynamic and pharmacokinetic characteristics of IL-10 in a mammalian subject, an initial trough concentration (achieved, for example, through the administration of one or more loading doses followed by a series of maintenance doses) gradually but continually decreases over a period of time even when the dosing parameters (e.g., amount and frequency) are kept constant. After that period to time, the gradual but continual decrease ends and a steady state serum trough concentration is maintained.

By way of example, parenteral administration (e.g., SC and IV) of ~0.1 mg/kg/day of an IL-10 agent (e.g., mIL-10) to a mouse (e.g., a C57BL/6 mouse) is required to maintain a steady state serum trough concentration of 2.0 ng/mL. However, that steady state serum trough concentration cannot be achieved until approximately 30 days after initiation of dosing at 0.1 mg/kg/day (and also after any loading dose(s)). Rather, after an initial serum trough concentration has been achieved (e.g., 2.5 ng/mL), that concentration gradually but continually decreases over the course of, for example, the approximately 30-day period, after which time the desired steady state serum trough concentration (2.0 ng/mL) is maintained. One of skill in the art will be able to determine the dose needed to maintain the desired steady state trough concentration using, for example, ADME and patient-specific parameters.

The present disclosure contemplates methods wherein the IL-10 agent comprises at least one modification to form a modified IL-10 agent, wherein the modification does not alter the amino acid sequence of the IL-10 agent. In some embodiments, the modified IL-10 agent is a PEG-IL-10 agent. The PEG-IL-10 agent can comprise at least one PEG molecule covalently attached to at least one amino acid residue of at least one subunit of IL-10 or comprise a mixture of mono-pegylated and di-pegylated IL-10 in other embodiments. The PEG component of the PEG-IL-10 agent can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa.

In some embodiments, the modified IL-10 agent comprises at least one Fc fusion molecule, at least one serum albumin (e.g., HSA or BSA), an HSA fusion molecule or an albumin conjugate. In additional embodiments, the modified IL-10 agent is glycosylated, is hesylated, or comprises at least one albumin binding domain. Some modified IL-10 agents can comprise more than one type of modification. In particular embodiments, the modification is site-specific. Some embodiments comprise a linker. Modified IL-10 agents are discussed in detail hereafter. The present disclosure also contemplates the use of CAR-T cell therapy for the treatment or prevention of a disease, disorder or condition (e.g., a cancer-related disorder) in a subject in conjunction with the introduction to the subject of cells genetically modified to express an IL-10 agent. Due to its the direct and local effect, the amount of the IL-10 agent secreted from such cells that is necessary to dampen the induction of antigen-specific toxicities targeting normal tissues expressing the target-antigen, and the extreme potency of CAR-T cell treatments resulting in life-threatening cytokine-release syndromes, is much less than the amount of an IL-10 agent administered to a subject in a conventional manner (e.g., subcutaneously). Indeed, the amount of the secreted IL-10 agent necessary to achieve the aforementioned effects may be undetectable in the serum.

In some such embodiments, the present disclosure contemplates a method of modulating a T cell-mediated immune response to a target cell population in a subject, comprising introducing to the subject a therapeutically effective plurality of cells genetically modified to express a) a chimeric antigen receptor, wherein the chimeric antigen receptor comprises at least one antigen-specific targeting region capable of binding to the target cell population, and wherein the binding of the chimeric antigen receptor targeting region to the target cell population is capable of eliciting activation-induced cell death; and b) an IL-10 agent in an amount sufficient to prevent or limit the activation-induced cell death.

In some embodiments, the chimeric antigen receptor and the IL-10 agent are expressed by the same vector, while in other embodiments the chimeric antigen receptor and the IL-10 agent are expressed by different vectors. In particular embodiments, the therapeutically effective plurality of cells is transfected with a vector that expresses the IL-10 agent in an amount sufficient to enhance cytotoxic function. The vector may be, for example, a plasmid or a viral vector. The present disclosure also contemplates the use of any other means of expressing the IL-10 agent. In particular embodiments, expression of the IL-10 agent is modulated by an expression control element.

In the embodiments described above, the plurality of cells may be obtained from the subject and genetically modified ex vivo. The plurality of cells is obtained from the subject by an aphaeretic process in some embodiments. In other embodiments of the present disclosure, the plurality of cells is memory CD8+ T cells, while in still other embodiments they are autologous tumor cells.

The present disclosure contemplates methods of modulating a T cell-mediated immune response to a target cell population in a subject, comprising introducing to the subject a) a therapeutically effective first plurality of cells genetically modified to express a chimeric antigen receptor, wherein the chimeric antigen receptor comprises at least one antigen-specific targeting region capable of binding to the target cell population, and wherein the binding of the chimeric antigen receptor targeting region to the cell population is capable of eliciting activation-induced cell death; and b) a therapeutically effective second plurality of cells genetically modified to express an IL-10 agent in an amount sufficient to prevent or limit the activation-induced cell death.

In particular embodiments, the therapeutically effective plurality of cells is transfected with a vector that expresses the IL-10 agent in an amount sufficient to enhance cytotoxic function. The therapeutically effective second plurality of cells comprises CD8+ T cells transfected with a vector that expresses the IL-10 agent in still other embodiments.

In particular embodiments, the first plurality of cells is obtained from the subject and genetically modified ex vivo, while in other embodiments the second plurality of cells is obtained from the subject and genetically modified ex vivo. The present disclosure contemplates embodiments wherein the first plurality of cells and the second plurality of cells are obtained from the subject by an aphaeretic process. In some embodiments, the first plurality of cells is memory CD8+ T cells, and the second plurality of cells is naïve CD8+ T cells. The first plurality of cells and the second plurality of cells are autologous tumor cells in still other embodiments.

In each of the aforementioned embodiments, the target cell population may comprise a tumor antigen. Vigneron, N. et al. ((15 Jul. 2013) Cancer Immunity 13:15) describe a database of T cell-defined human tumor antigens containing over 400 tumor antigenic peptides. Examples of tumor antigens include, but are not limited to, CD19, CD20, CD22, ROR1, mesothelin, CD33/IL3Ra, c-Met, PSMA, Glycolipid F77, EGFRvIII, GD-2, NY-ESO-1 TCR, MAGE A3 TCR, or any combination thereof.

The present disclosure also contemplates the use of CAR-T cell therapy for the treatment or prevention of a disease, disorder or condition (e.g., a cancer-related disorder) in a subject in combination with the administration of an IL-10 agent (e.g., PEG-IL-10) or the introduction of a vector that expresses an IL-10 agent.

A particular embodiment comprises methods of treating a subject having a cancer-related disease, disorder or condition (e.g., a tumor), comprising a) introducing to the subject a therapeutically effective plurality of cells genetically modified to express a chimeric antigen receptor, wherein the chimeric antigen receptor comprises at least one antigen-specific targeting region capable of binding to the target cell population, and wherein the binding of the chimeric antigen receptor targeting region to the target cell population is capable of eliciting activation-induced cell death; and b) administering to the subject a therapeutically effective amount of an IL-10 agent sufficient to prevent or limit the activation-induced cell death. In particular embodiments, the subject being treated has an immune-related disease, disorder or condition or another disease, disorder or condition described herein.

In certain embodiments of the present disclosure, such methods are used in therapeutic protocols for the prevention of a cancer-related disease, disorder or condition in a subject, while in other embodiments such methods are used in therapeutic protocols for the prevention of immune-related disorders. Further aspects of the above-described methods, including dosing parameters and regimens for the IL-10 agents as well as exemplary types of such agents, are described elsewhere herein.

Additional embodiments of the present disclosure contemplate methods of treating a subject having a cancer-related disease, disorder or condition, comprising introducing to the subject a therapeutically effective plurality of cells genetically modified to express a) a chimeric antigen receptor, wherein the chimeric antigen receptor comprises at least one antigen-specific targeting region capable of binding to the target cell population, and wherein the binding of the chimeric antigen receptor targeting region to the target cell population is capable of eliciting activation-induced cell death; and b) an IL-10 agent in an amount sufficient to prevent or limit the activation-induced cell death.

In some embodiments, the chimeric antigen receptor and the IL-10 agent are expressed by the same vector, while in other embodiments the chimeric antigen receptor and the IL-10 agent are expressed by different vectors. In particular embodiments, the therapeutically effective plurality of cells is transfected with a vector that expresses the IL-10 agent in an amount sufficient to enhance cytotoxic function. The vector may be, for example, a plasmid or a viral vector. The present disclosure also contemplates the use of any other means of expressing the IL-10 agent. In particular embodiments, expression of the IL-10 agent is modulated by an expression control element.

In the embodiments described above, the plurality of cells may be obtained from the subject and genetically modified ex vivo. According to the present disclosure, the plurality of cells is obtained from the subject by an aphaeretic process in some embodiments. The plurality of cells is memory CD8+ T cells in particular embodiments, and is autologous tumor cells in other embodiments.

The present disclosure contemplates methods wherein the IL-10 agent is expressed in an amount sufficient to prevent or limit the activation-induced cell death at least one week after introduction to the subject. In other particular embodiments, the IL-10 agent is expressed in an amount sufficient to prevent or limit the activation-induced cell death at least two weeks, at least three weeks, at least one month, at least two months, at least three months, at least four months, at least five months, at least six months, at least seven months, at least eight months, at least nine months, or at least one year or more, after introduction to the subject.

Still further embodiments of the present disclosure contemplate methods of treating a subject having a cancer-related disease, disorder or condition, comprising introducing to the subject a) a therapeutically effective first plurality of cells genetically modified to express a chimeric antigen receptor, wherein the chimeric antigen receptor comprises at least one antigen-specific targeting region capable of binding to the target cell population, and wherein the binding of the chimeric antigen receptor targeting region to the target cell population is capable of eliciting activation-induced cell death; and b) a therapeutically effective second plurality of cells genetically modified to express an IL-10 agent in an amount sufficient to prevent or limit the activation-induced cell death. Examples of the lengths of time which the IL-10 agent is expressed in an amount sufficient to prevent or limit the activation-induced cell death are described elsewhere herein.

In certain embodiments, the methods described above are used in therapeutic protocols for the prevention of a disease, disorder or condition, including a cancer- or an immune-related disease, disorder or condition in a subject.

The present disclosure contemplates methods wherein the IL-10 agent is expressed in an amount sufficient to prevent or limit the activation-induced cell death for periods of time described elsewhere herein.

In particular embodiments, the therapeutically effective first plurality of cells is transfected with a vector that expresses the IL-10 agent in an amount sufficient to enhance cytotoxic function. The therapeutically effective second plurality of cells comprises CD8+ T cells transfected with a vector that expresses the IL-10 agent in still other embodiments.

In particular embodiments, the first plurality of cells is obtained from the subject and genetically modified ex vivo, while in other embodiments the second plurality of cells is obtained from the subject and genetically modified ex vivo. The present disclosure contemplates embodiments wherein the first plurality of cells and the second plurality of cells are obtained from the subject by an aphaeretic process. In some embodiments, the first plurality of cells is memory CD8+ T cells, and the second plurality of cells is naïve CD8+ T cells. The first plurality of cells and the second plurality of cells are autologous tumor cells in still other embodiments.

In each of the aforementioned embodiments, the target cell population may comprise a tumor antigen, examples of which are described elsewhere herein.

The present disclosure contemplates nucleic acid molecules that encode the IL-10 agents described herein. In certain embodiments, a nucleic acid molecule is operably linked to an expression control element that confers expression of the nucleic acid molecule encoding the IL-10 agent. In some embodiments, a vector (e.g., a plasmid or a viral vector) comprises the nucleic acid molecule. Also contemplated herein are transformed or host cells that express the IL-10 agent.

In still further embodiments, the present disclosure provides methods of enhancing the function of a CAR-T T cell, comprising a) genetically engineering a T cell to express a CAR, thereby generating a CAR-T T cell; and b) modulating the CAR-T T cell with an agent (e.g., a small interfering RNA (siRNA)) that reduces the amount of at least one cytokine secreted by the CAR-T T cell. Examples of cytokines include, but are not limited to, members of the tumor necrosis factor family or the transforming growth factor beta superfamily (e.g., TGF-β). Embodiments are contemplated wherein reducing the amount of TGF-β reduces the proliferation of T regulatory cells.

Other embodiments will be apparent to the skilled artisan based on the teachings of the present disclosure.

DETAILED DESCRIPTION

Figure 1:
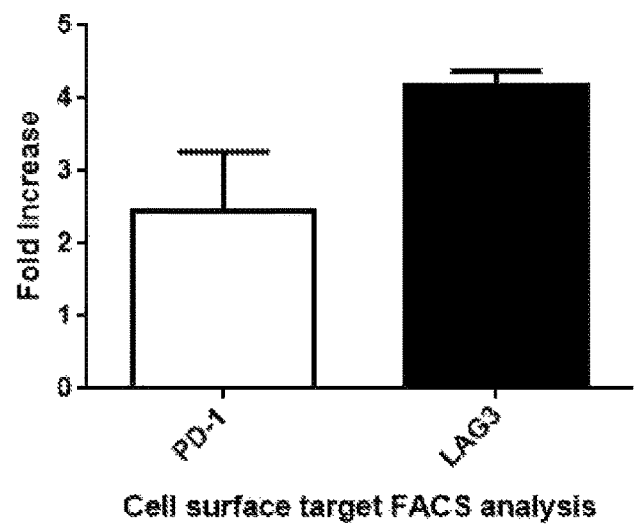
FIG. 1 depicts the fold-increase of PD-1 and LAG3+ peripheral T cells after 29 days of treatment with PEG-rHuIL-10.

Before the present disclosure is further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

Overview

CAR-T T cell therapy is a promising therapeutic approach for, for example, the treatment of cancer-related (e.g., B and T cell lymphomas) and immune-related malignancies. CAR-T T cells generally comprise patient-derived memory CD8+ T cells modified to express a recombinant T cell receptor specific for a known antigen present on, for example, a tumor of interest. While the present disclosure is generally described in the context of using CAR-T cell therapy for the treatment of cancer, it is to be understood that such therapy also finds utility in the treatment of other indications.

As discussed further herein, when CAR-T cell therapy has been used in the treatment of certain cancers (e.g., non-B cell malignancies), high affinity T cell receptor interactions with significant antigen burden have been observed that can lead to activation-induced cell death. Although IL-10 has previously been linked to the enhancement of activation-induced cell death, the data presented herein suggest that an IL-10 agent may be used in conjunction with CAR-T T cell therapy to prevent or limit activation-induced cell death while enhancing CD8+ T cell function and survival.

It should be noted that any reference to "human" in connection with the polypeptides and nucleic acid molecules of the present disclosure is not meant to be limiting with respect to the manner in which the polypeptide or nucleic acid is obtained or the source, but rather is only with reference to the sequence as it can correspond to a sequence of a naturally occurring human polypeptide or nucleic acid molecule. In addition to the human polypeptides and the nucleic acid molecules which encode them, the present disclosure contemplates IL-10-related polypeptides and corresponding nucleic acid molecules from other species.

Definitions

Unless otherwise indicated, the following terms are intended to have the meaning set forth below. Other terms are defined elsewhere throughout the specification.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, IL-10 or PEG-IL-10), a nucleic acid (e.g., a nucleic acid encoding native human IL-10); a pharmaceutical composition comprising the foregoing, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering IL-10 or a pharmaceutical composition comprising IL-10) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease. The terms may also be used in other contexts, such as situations where IL-10 or PEG-IL-10 contacts an IL-10 receptor in, for example, the fluid phase or colloidal phase.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering IL-10 or a pharmaceutical composition comprising IL-10) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based upon a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the amount of inflammatory cytokines produced following administration can be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration of IL-10) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule can be more permeable to cells, less susceptible to degradation, and less likely to elicit an immune response than large molecules.

The term "ligand" refers to, for example, peptide, polypeptide, membrane-associated or membrane-bound molecule, or complex thereof, that can act as an agonist or antagonist of a receptor. "Ligand" encompasses natural and synthetic ligands, e.g., cytokines, cytokine variants, analogs, muteins, and binding compositions derived from antibodies. "Ligand" also encompasses small molecules, e.g., peptide mimetics of cytokines and peptide mimetics of antibodies. The term also encompasses an agent that is neither an agonist nor antagonist, but that can bind to a receptor without significantly influencing its biological properties, e.g., signaling or adhesion. Moreover, the term includes a membrane-bound ligand that has been changed, e.g., by chemical or recombinant methods, to a soluble version of the membrane-bound ligand. A ligand or receptor can be entirely intracellular, that is, it can reside in the cytosol, nucleus, or some other intracellular compartment. The complex of a ligand and receptor is termed a "ligand-receptor complex."

The terms "inhibitors" and "antagonists", or "activators" and "agonists", refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor can also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of an IL-10 agent (or the nucleic acid molecules encoding them), either directly or indirectly; or to enhance the ability of a molecule to produce an effect comparable to that of an IL-10 agent. The term "modulator" is meant to refer broadly to molecules that can effect the activities described above. By way of example, a modulator of, e.g., a gene, a receptor, a ligand, or a cell, is a molecule that alters an activity of the gene, receptor, ligand, or cell, where activity can be activated, inhibited, or altered in its regulatory properties. A modulator can act alone, or it can use a cofactor, e.g., a protein, metal ion, or small molecule. The term "modulator" includes agents that operate through the same mechanism of action as IL-10 (i.e., agents that modulate the same signaling pathway as IL-10 in a manner analogous thereto) and are capable of eliciting a biological response comparable to (or greater than) that of IL-10.

Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule can describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term can also refer to activity in modulating or maintaining cell-to-cell interactions (e.g., adhesion), or activity in maintaining a structure of a cell (e.g., a cell membrane). "Activity" can also mean specific activity, e.g., [catalytic activity]/[mg protein], or [immunological activity]/[mg protein], concentration in a biological compartment, or the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect can refer to efficacy, stability, solubility, or immunogenicity.

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences; fusion proteins with or without N-terminus methionine residues; fusion proteins with immunologically tagged proteins; and the like.

It will be appreciated that throughout this disclosure reference is made to amino acids according to the single letter or three letter codes. For the reader's convenience, the single and three letter amino acid codes are provided below:

| G | Glycine | Gly | P | Proline | Pro |
|---|---|---|---|---|---|
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

As used herein, the term "variant" encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Non-naturally-occurring variants include polypeptides and nucleic acids that comprise a change in amino acid or nucleotide sequence, respectively, where the change in sequence is artificially introduced (e.g., muteins); for example, the change is generated in the laboratory by human intervention ("hand of man"). Thus, herein a "mutein" refers broadly to mutated recombinant proteins that usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from", in the context of an amino acid sequence or polynucleotide sequence (e.g., an amino acid sequence "derived from" an IL-10 polypeptide), is meant to indicate that the polypeptide or nucleic acid has a sequence that is based on that of a reference polypeptide or nucleic acid (e.g., a naturally occurring IL-10 polypeptide or an IL-10-encoding nucleic acid), and is not meant to be limiting as to the source or method in which the protein or nucleic acid is made. By way of example, the term "derived from" includes homologs or variants of reference amino acid or DNA sequences.

In the context of a polypeptide, the term "isolated" refers to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was made by either synthetic or recombinant means.

"Enriched" means that a sample is non-naturally manipulated (e.g., by a scientist) so that a polypeptide of interest is present in a) a greater concentration (e.g., at least 3-fold greater, at least 4-fold greater, at least 8-fold greater, at least 64-fold greater, or more) than the concentration of the polypeptide in the starting sample, such as a biological sample (e.g., a sample in which the polypeptide naturally occurs or in which it is present after administration), or b) a concentration greater than the environment in which the polypeptide was made (e.g., as in a bacterial cell).

"Substantially pure" indicates that a component (e.g., a polypeptide) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

IL-10 and PEG-IL-10

The anti-inflammatory cytokine IL-10, also known as human cytokine synthesis inhibitory factor (CSIF), is classified as a type(class)-2 cytokine, a set of cytokines that includes IL-19, IL-20, IL-22, IL-24 (Mda-7), and IL-26, interferons (IFN-α, -β, -γ, -δ, -ε, -κ, -Ω, and -τ) and interferon-like molecules (limitin, IL-28A, IL-28B, and IL-29).

IL-10 is a cytokine with pleiotropic effects in immunoregulation and inflammation. It is produced by mast cells, counteracting the inflammatory effect that these cells have at the site of an allergic reaction. While it is capable of inhibiting the synthesis of pro-inflammatory cytokines such as IFN-γ, IL-2, IL-3, TNFα and GM-CSF, IL-10 is also stimulatory towards certain T cells and mast cells and stimulates B-cell maturation, proliferation and antibody production. IL-10 can block NF-κB activity and is involved in the regulation of the JAK-STAT signaling pathway. It also induces the cytotoxic activity of CD8+ T-cells and the antibody production of B-cells, and it suppresses macrophage activity and tumor-promoting inflammation. The regulation of CD8+ T-cells is dose-dependent, wherein higher doses induce stronger cytotoxic responses.

Human IL-10 is a homodimer with a molecular mass of 37 kDa, wherein each 18.5 kDa monomer comprises 178 amino acids, the first 18 of which comprise a signal peptide, and two cysteine residues that form two intramolecular disulfide bonds. The IL-10 dimer becomes biologically inactive upon disruption of the non-covalent interactions between the two monomer subunits.

The present disclosure contemplates human IL-10 (NP_000563) and murine IL-10 (NP_034678), which exhibit 80% homology, and use thereof. In addition, the scope of the present disclosure includes IL-10 orthologs, and modified forms thereof, from other mammalian species, including rat (accession NP_036986.2; GI 148747382); cow (accession NP_776513.1; GI 41386772); sheep (accession NP_001009327.1; GI 57164347); dog (accession ABY86619.1; GI 166244598); and rabbit (accession AAC23839.1; GI 3242896).

As alluded to above, the terms "IL-10", "IL-10 polypeptide(s)", "IL-10 molecule(s)", "IL-10 agent(s)" and the like are intended to be broadly construed and include, for example, human and non-human IL-10-related polypeptides, including homologs, variants (including muteins), and fragments thereof, as well as IL-10 polypeptides having, for example, a leader sequence (e.g., the signal peptide), and modified versions of the foregoing. In further particular embodiments, IL-10, IL-10 polypeptide(s), and IL-10 agent(s) are agonists.

The IL-10 receptor, a type II cytokine receptor, consists of alpha and beta subunits, which are also referred to as R1 and R2, respectively. Receptor activation requires binding to both alpha and beta. One homodimer of an IL-10 polypeptide binds to alpha and the other homodimer of the same IL-10 polypeptide binds to beta.

The utility of recombinant human IL-10 is frequently limited by its relatively short serum half-life, which can be due to, for example, renal clearance, proteolytic degradation and monomerization in the blood stream. As a result, various approaches have been explored to improve the pharmacokinetic profile of IL-10 without disrupting its dimeric structure and thus adversely affecting its activity. Pegylation of IL-10 results in improvement of certain pharmacokinetic parameters (e.g., serum half-life) and/or enhancement of activity.

As used herein, the terms "pegylated IL-10" and "PEG-IL-10" refer to an IL-10 molecule having one or more polyethylene glycol molecules covalently attached to at least one amino acid residue of the IL-10 protein, generally via a linker, such that the attachment is stable. The terms "monopegylated IL-10" and "mono-PEG-IL-10" indicate that one polyethylene glycol molecule is covalently attached to a single amino acid residue on one subunit of the IL-10 dimer, generally via a linker. As used herein, the terms "dipegylated IL-10" and "di-PEG-IL-10" indicate that at least one polyethylene glycol molecule is attached to a single residue on each subunit of the IL-10 dimer, generally via a linker.

In certain embodiments, the PEG-IL-10 used in the present disclosure is a mono-PEG-IL-10 in which one to nine PEG molecules are covalently attached via a linker to the alpha amino group of the amino acid residue at the N-terminus of one subunit of the IL-10 dimer. Monopegylation on one IL-10 subunit generally results in a non-homogeneous mixture of non-pegylated, monopegylated and dipegylated IL-10 due to subunit shuffling. Moreover, allowing a pegylation reaction to proceed to completion will generally result in non-specific and multi-pegylated IL-10, thus reducing its bioactivity. Thus, particular embodiments of the present disclosure comprise the administration of a mixture of mono- and di-pegylated IL-10 produced by the methods described herein.

In particular embodiments, the average molecular weight of the PEG moiety is between about 5 kDa and about 50 kDa. Although the method or site of PEG attachment to IL-10 is not critical, in certain embodiments the pegylation does not alter, or only minimally alters, the activity of the IL-10 agent. In certain embodiments, the increase in half-life is greater than any decrease in biological activity. The biological activity of PEG-IL-10 is typically measured by assessing the levels of inflammatory cytokines (e.g., TNF-α or IFN-γ) in the serum of subjects challenged with a bacterial antigen (lipopolysaccharide (LPS)) and treated with PEG-IL-10, as described in U.S. Pat. No. 7,052,686.

IL-10 variants can be prepared with various objectives in mind, including increasing serum half-life, reducing an immune response against the IL-10, facilitating purification or preparation, decreasing conversion of IL-10 into its monomeric subunits, improving therapeutic efficacy, and lessening the severity or occurrence of side effects during therapeutic use. The amino acid sequence variants are usually predetermined variants not found in nature, although some can be post-translational variants, e.g., glycosylated variants. Any variant of IL-10 can be used provided it retains a suitable level of IL-10 activity.

The phrase "conservative amino acid substitution" refers to substitutions that preserve the activity of the protein by replacing an amino acid(s) in the protein with an amino acid with a side chain of similar acidity, basicity, charge, polarity, or size of the side chain. Conservative amino acid substitutions generally entail substitution of amino acid residues within the following groups: 1) L, I, M, V, F; 2) R, K; 3) F, Y, H, W, R; 4) G, A, T, S; 5) Q, N; and 6) D, E. Guidance for substitutions, insertions, or deletions can be based on alignments of amino acid sequences of different variant proteins or proteins from different species. Thus, in addition to any naturally-occurring IL-10 polypeptide, the present disclosure contemplates having 1, 2, 3, 4, 5, 6, 7, 8, 9, or 10 usually no more than 20, 10, or 5 amino acid substitutions, where the substitution is usually a conservative amino acid substitution.

The present disclosure also contemplates active fragments (e.g., subsequences) of mature IL-10 containing contiguous amino acid residues derived from the mature IL-10. The length of contiguous amino acid residues of a peptide or a polypeptide subsequence varies depending on the specific naturally-occurring amino acid sequence from which the subsequence is derived. In general, peptides and polypeptides can be from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

Additionally, IL-10 polypeptides can have a defined sequence identity compared to a reference sequence over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a suitable IL-10 polypeptide can comprise an amino acid sequence having at least about 75%, at least about 80%, at least about 85%, at least about 90%, at least about 95%, at least about 98%, or at least about 99%, amino acid sequence identity to a contiguous stretch of from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

As discussed further below, the IL-10 polypeptides can be isolated from a natural source (e.g., an environment other than its naturally-occurring environment) and can also be recombinantly made (e.g., in a genetically modified host cell such as bacteria, yeast, Pichia, insect cells, and the like), where the genetically modified host cell is modified with a nucleic acid comprising a nucleotide sequence encoding the polypeptide. The IL-10 polypeptides can also be synthetically produced (e.g., by cell-free chemical synthesis).

Nucleic acid molecules encoding the IL-10 agents are contemplated by the present disclosure, including their naturally-occurring and non-naturally occurring isoforms, allelic variants and splice variants. The present disclosure also encompasses nucleic acid sequences that vary in one or more bases from a naturally-occurring DNA sequence but still translate into an amino acid sequence that corresponds to an IL-10 polypeptide due to degeneracy of the genetic code.

Chimeric Antigen Receptor T Cells

Chimeric antigen receptor T cells (CARs; also known as artificial T cell receptors, chimeric T cell receptors, and chimeric immunoreceptors) represent an emerging therapy for cancer (e.g., treatment of B and T cell lymphomas) and other malignancies. CAR-T T cells generally comprise patient-derived memory CD8+ T cells modified to express a recombinant T cell receptor specific for a known antigen present on, for example, a tumor of interest. Other types of T cells contemplated herein include naïve T cells, central memory T cells, effector memory T cells or combination thereof. While the present disclosure is generally described in the context of using CAR-T cell therapy for the treatment of cancer, it is to be understood that such therapy is not so limited.

CAR-T T cell therapy comprises use of adoptive cell transfer (ACT). ACT, which utilizes a patient's own cultured T cells, has shown promise as a patient-specific cancer therapy (Snook and Waldman (2013) Discov Med 15(81): 120-25). The use of genetic engineering approaches to insert antigen-targeted receptors of defined specificity into T cells has greatly extended the potential capabilities of ACT. In most instances, these engineered chimeric antigen receptors are used to graft the specificity of a monoclonal antibody onto a T cell.

The initiation of CAR-T cell therapy comprises the removal of T cells from a patient. The T cells are then genetically engineered to express CARs directed towards antigens specific for a known cancer (e.g., a tumor). Following amplification ex vivo to a sufficient number, the autologous cells are infused back into the patient, resulting in the antigen-specific destruction of the cancer.

CARs are a type of antigen-targeted receptor composed of intracellular T-cell signaling domains generally fused to extracellular tumor-binding moieties, most commonly single-chain variable fragments (scFvs) from monoclonal antibodies. CARs directly recognize cell surface antigens, independent of MHC-mediated presentation, permitting the use of a single receptor construct specific for any given antigen in all patients.

Chimeric antigen receptors generally comprise several primary components, some of which are described hereafter.

As used herein, the phrase "antigen-specific targeting region" (ASTR) refers to the region that directs the CAR to specific antigens. The targeting regions on the CAR are extracellular. In particular embodiments of the present disclosure, the CARs comprise at least two targeting regions which target at least two different antigens. In further particular embodiments, the CARs comprise three or more targeting regions which target at least three or more different antigens. In some embodiments, the antigen-specific targeting regions comprise an antibody or a functional equivalent thereof or a fragment thereof or a derivative thereof, and each of the targeting regions targets a different antigen. The targeting regions may comprise full-length heavy chain, Fab fragments, single chain Fv (scFv) fragments, divalent single chain antibodies or diabodies, each of which are specific to the target antigen. In certain aspects of the present disclosure, the targeting regions may comprise linked cytokines, ligand binding domains from naturally occurring receptors, soluble protein-peptide ligands for a receptor, peptides, affibodies and vaccines to prompt an immune response. The skilled artisan is aware of other molecules that can be used as an antigen-specific targeting region.

As used herein, the term "extracellular spacer domain" (ESD) refer to the hydrophilic region between the antigen-specific targeting region and the transmembrane domain. The present disclosure contemplates embodiments wherein the CARs comprise an ESD, examples of which include Fc Ab fragments, or fragments or derivatives thereof, hinge regions of antibodies or fragments or derivatives thereof; CH2 or CH3 regions of antibodies; artificial spacer sequences, including Gly3 or CH1 and CH3 domains of IgGs (such as human IgG4); or combinations of the foregoing. One of ordinary skill in the art is aware of other ESDs, which are contemplated herein.

As used herein, the term "transmembrane domain" (TMD) refers to the region of the CAR which traverses the plasma membrane. In some embodiments, the transmembrane region is a transmembrane protein (e.g., a Type I transmembrane protein), an artificial hydrophobic sequence, or a combination thereof. The skilled artisan is aware of other transmembrane domains which may be used in conjunction with the teachings of the present disclosure.

As used herein, the terms "intracellular signaling domain" (ISD) and "cytoplasmic domain" refer to the portion of the CAR which transduces the effector function signal and directs the cell to perform its specialized function. Examples of ISDs include the zeta chain of the T-cell receptor complex or any of its homologs (e.g., eta. chain, FcεR1γ and β chains, MB1 (Igα) chain, B29 (Igβ) chain, etc.), human CD3 zeta chain, CD3 polypeptides (δ, Δ and ε), syk family tyrosine kinases (Syk, ZAP 70, etc.), src family tyrosine kinases (Lck, Fyn, Lyn, etc.) and other molecules involved in T-cell transduction, such as CD2, CD5 and CD28. The skilled artisan is aware of other ISDs that may be used in conjunction with the teachings of the present disclosure.

The term "co-stimulatory domain" (CSD) refers to the portion of the CAR which enhances the proliferation, survival or development of memory cells. As indicated elsewhere herein, the CARs of the present disclosure may comprise one or more co-stimulatory domains. In some embodiments of the present disclosure, the CSD comprises one or more of members of the TNFR superfamily, CD28, CD137 (4-1BB), CD134 (OX40), Dap10, CD27, CD2, CD5, ICAM-1, LFA-1 (CD11a/CD18), Lck, TNFR-I, TNFR-II, Fas, CD30, CD40 or combinations thereof. The ordinarily skilled artisan is aware of other co-stimulatory domains that may be used in conjunction with the teachings of the present disclosure.

As used in conjunction with the CAR-T T cell technology described herein, the terms "linker", "linker domain" and "linker region" refer to an oligo- or polypeptide region from about 1 to 100 amino acids in length, which links together any of the domains/regions of the CAR of the disclosure. Linkers may be composed of flexible residues like glycine and serine so that the adjacent protein domains are free to move relative to one another. Certain embodiments comprise the use of linkers of longer length when it is desirable to ensure that two adjacent domains do not sterically interfere with each another. In some embodiments, the linkers are non-cleavable, while in others they are cleavable (e.g., 2A linkers (for example T2A)), 2A-like linkers or functional equivalents thereof, and combinations of the foregoing. Embodiments of the present disclosure are contemplated wherein the linkers include the picornaviral 2A-like linker, CHYSEL sequences of porcine teschovirus (P2A), Thosea asigna virus (T2A), or combinations, variants and functional equivalents thereof. In still further embodiments, the linker sequences comprise Asp-Val/Ile-Glu-X-Asn-Pro-Gly$^{(2A)}$-pro$^{(2B)}$ motif, which results in cleavage between the 2A glycine and the 2B proline. Other linkers will be readily apparent to the skilled artisan and are contemplated for use with the teachings of the present disclosure.

There has been a relatively rapid progression of CAR-T T cell therapy (see generally, US Patent Appln Publn No 20150038684). First generation CARs were directed to fusion of antigen-recognition domains to the CD3ζ activation chain of the T-cell receptor (TCR) complex. While these first generation CARs induced T-cell effector function in vitro, in vivo efficacy was largely limited by their poor antitumor efficacy. Evolution of CAR technology resulted in second generation CARs, which include the CD3ζ activation chain in tandem with one CSD, examples of which include intracellular domains from CD28 or a variety of TNF receptor family molecules such as 4-1BB (CD137) and OX40 (CD134). Third generation CARs have been developed that include two costimulatory signals in addition to the CD3ζ activation chain, the CSDs most commonly being from CD28 and 4-1BB. Second and third generation CARs dramatically improved antitumor efficacy. However, it is not entirely clear if specific combinations of costimulatory molecules are advantageous over others. Moreover, the increased potency of second and third generation CARs, coupled with the lack of truly tumor-specific antigen-targets, has also increased the risk of severe toxicities. (See, e.g., Carpenito et al. (2009) Proc Natl Acad Sci USA 106(9): 3360-65; Grupp et al. (2013) N Engl J Med 368(16):1509-18).

Activation-Induced Cell Death

The infusion of genetically-modified T cells directed to specific target antigens has several potential benefits, including long-term disease control, rapid onset of action similar to that of cytotoxic chemotherapy or with targeted therapies, and circumvention of both immune tolerance of the T cell repertoire and MHC restriction. However, treatment of certain cancers (e.g., non-B cell malignancies) with CAR-T cell therapy has, in part, been limited by both the induction of antigen-specific toxicities targeting normal tissues expressing the target-antigen, and the extreme potency of CAR-T cell treatments, sometimes resulting in life-threatening cytokine-release syndromes (Magee (November 2014) Discov Med 18(100):265-71). In particular, it has been observed that high affinity T cell receptor interactions with significant antigen burden can lead to activation-induced cell death (Song et al. (2012) Blood 119(3):696-706; Hombach et al (2013) Mol Ther 21(12):2268-77).

Activation-induced cell death (AICD), programmed cell death that results from the interaction of Fas receptors (e.g., Fas, CD95) with Fas ligands (e.g., FasL, CD95 ligand), helps to maintain peripheral immune tolerance. The AICD effector cell expresses FasL, and apoptosis is induced in the cell expressing the Fas receptor. Activation-induced cell death is a negative regulator of activated T lymphocytes resulting from repeated stimulation of their T cell receptors. Alteration of this process may lead to autoimmune diseases (Zhang J, et al. (2004) Cell Mol Immunol. 1(3):186-92).

Mechanistically, the binding of a Fas ligand to a Fas receptor triggers trimerization of the Fas receptor, whose cytoplasmic domain is then able to bind the death domain of the adaptor protein FADD (Fas-associated protein with death domain). Procaspase 8 binds to FADD's death effector domain and proteolytically self-activates caspase 8; Fas, FADD, and procaspase 8 together form a death-inducing signaling complex. Activated caspase 8 is released into the cytosol, where it activates the caspase cascade that initiates apoptosis (Nagata S. (1997) Cell. 88(3):355-65s.

The balance of activation-induced proliferation and death of effector cells is a key point in the homeostatic expansion of T cells. While resting T cells are susceptible to apoptosis, stimulation of T cells through TCR/CD3 in the presence of cytokines (e.g., IL-2, IL-4, IL-7 and IL-12) results in clonal expansion. Interestingly, the roles of these molecules in the homeostasis of T cells are sometimes paradoxical. By way of example, IL-2 is necessary for proliferation and survival of CD4+ T cells, but it is also a prerequisite for activation-induced cell death. Moreover, IL-18 has been shown to promote expansion and survival of activated CD8+ T cells. IL-18 may influence immune/inflammatory responses by regulating the size of the CD8+ T cell population with specific functions following exposure to stimuli. Regulation of proliferation and activation-induced cell death of activated T cells is closely associated with immune/inflammatory responses (Li, W., et al. (July 2007) J Leukocyte Bio 82(1):142-51).

Effect of IL-10 on CAR-T T Cell Therapy

The characteristics of IL-10 agents (e.g., PEG-IL-10) are described elsewhere herein. As an anti-inflammatory and immunosuppressive molecule, IL-10 inhibits antigen presentation, CD4+ T cell function, CD8+ T cell pathogen-specific function (Biswas et al. (2007) J Immunol 179(7): 4520-28), viral epitope-specific CD8+ T cell IFNγ responses (Liu et al. (2003) J Immunol 171(9):4765-72), and anti-LCMV (Lymphocytic Choriomeningitis Virus) CD8+ T cell responses (Brooks et al. (2008) PNAS USA 105(51):20428-433).

While IL-10 has been discussed in the context of enhancement of activation-induced cell death (Georgescu et al. (1997) J Clin Invest 100(10):2622-33), in vitro and in vivo data presented herein indicate that an IL-10 agent (e.g., PEG-IL-10) may be combined with CAR-T T cell therapy to prevent or limit activation-induced cell death while enhancing CD8+ T cell function and survival.

By way of example, the findings presented in Example 1 of the Experimental section suggest that PEG-IL-10 administration mediated CD8+ T cell immune activation. As described in Example 1, the number of PD-1- and LAG3-expressing CD8+ T cells was compared in oncology patients before and after treatment with PEG-rHuIL-10 (see Example 1). Both PD-1 and LAG3 are markers of CD8+ T cell activation and cytotoxic function. The number of peripheral CD8+ T cells expressing PD-1 increased by ~2-fold, and the number of peripheral CD8+ T cells expressing LAG3 increased by ~4-fold. Taken as a whole, these data indicate that PEG-IL-10 administration mediated CD8+ T cell immune activation.

Administration of PEG-IL-10 was also observed to enhance the function of activated memory CD8+ T cells (see Example 2). Memory T cells (also referred to as antigen-experienced T cells) are a subset of T lymphocytes (e.g., helper T cells (CD4+) and cytotoxic T cells (CD8+)) that have previously encountered and responded to their cognate antigen during prior infection, exposure to cancer, or previous vaccination. In contrast, naïve T cells have not encountered their cognate antigen within the periphery; they are commonly characterized by the absence of the activation markers CD25, CD44 or CD69, and the absence of memory CD45RO isoform. Memory T cells, which are generally CD45RO+, are able to reproduce and mount a faster and stronger immune response than naïve T cells.

Because CAR-T T cells are derived from memory CD8+ T cells, the effect of PEG-IL-10 on memory CD8+ T cells was assessed in vitro. The data presented in Example 2 are consistent with the effect of PEG-IL-10 to enhance the function of activated memory CD8+ T cells.

Methods and Models

The present disclosure contemplates various methods and models for identifying candidate subject populations (or individual subjects) having undergone or suspected of having undergone activation-induced cell death as a result of CAR-T cell therapy that can be responsive to the therapies described herein. Such therapies include monotherapy with an IL-10 agent (e.g., PEG-IL-10) and combination therapy with an IL-10 agent and one or more distinct agents that have been shown to exhibit beneficial activity in preventing or limiting activation-induced cell death. In some embodiments, the methods and models allow a determination of whether administration of and IL-10 agent achieves the desired level of a reduction in activation-induced cell death or whether a combination of an IL-10 agent and another agent is more beneficial. In other embodiments, the methods and models allow a determination of whether administration of the combination results in fewer undesirable effects.

Certain embodiments of the present disclosure comprise the use of in vitro, ex vivo and in vivo methods and/or models. The subject population (or individual subject) is a non-human animal (e.g., rodent) or human in certain embodiments of the present disclosure.

By way of example, but not limitation, one aspect of the present disclosure contemplates a method for determining whether a test subject having undergone or suspected of having undergone activation-induced cell death is a candidate for treatment with an of IL-10 agent (e.g., PEG-IL-10), the method comprising a) providing a test subject having an indicia of activation-induced cell death, b) administering the IL-10 agent to the test subject in an amount sufficient to achieve a desired response in a reference population, and c) determining whether the test subject exhibits the desired response; wherein the determination of the desired response indicates that the test subject is a candidate for treatment. The skilled artisan is able to modify such methods for use with combination therapy. The desired response can be any result deemed favorable under the circumstances.

As indicated above, the present disclosure also contemplates various models. Any model can be used that provides reliable, reproducible results. The skilled artisan is familiar with models that can be used in conjunction with the subject matter of the present disclosure; in one embodiment, the IL-10 agent (e.g., PEG-IL-10) is evaluated in a model comprising a non-human subject (e.g., a mouse). Particular embodiments of the present disclosure contemplate a model for determining whether an IL-10 agent, in combination with or without another agent, is a candidate for preventing or reducing activation-induced cell death.

Further embodiments of the present disclosure comprise a method or model for determining the optimum amount of an IL-10 agent, in combination with or without another agent. An optimum amount can be, for example, an amount that achieves an optimal effect in a subject or subject population. By manipulating the amounts of the agent(s), a clinician is able to determine the optimal dosing regimen for preventing or reducing activation-induced cell death.

Biomarkers

The present disclosure also contemplates the use of biomarkers in conjunction with the methods and models described herein. The term "biomarker(s)" refers to a characteristic that is objectively measured and evaluated as an indicator of normal biological processes, pathogenic processes, or pharmacologic responses to a therapeutic intervention. The indicator may be any substance, structure, or process that can be measured in the body or its products and influences or predicts the incidence of outcome or disease.

In some embodiments of the present disclosure, a biomarker(s) is used to predict a clinical response(s) to therapy with an IL-10 agent (e.g., PEG-IL-10). In some instances, a pre-treatment biomarker can be used in such therapy wherein the biomarker has been validated to the point at which it could be applied as part of standard-of-care therapeutic decision-making.

Serum Concentrations

The blood plasma levels of IL-10 in the methods described herein can be characterized in several manners, including: (1) a mean IL-10 serum trough concentration above some specified level or in a range of levels; (2) a mean IL-10 serum trough concentration above some specified level for some amount of time; (3) a steady state IL-10 serum concentration level above or below some specified level or in a range of levels; or (4) a $C_{max}$ of the concentration profile above or below some specified level or in some range of levels. As set forth herein, mean serum trough IL-10 concentrations have been found to be of particular import for efficacy in certain indications.

In some embodiments of the present disclosure, blood plasma and/or serum level concentration profiles that can be produced include: a mean IL-10 plasma and/or serum trough concentration of greater than about 1.0 pg/mL, greater than about 10.0 pg/mL, greater than about 20.0 pg/mL, greater than about 30 pg/mL, greater than about 40 pg/mL, greater than about 50.0 pg/mL, greater than about 60.0 pg/mL, greater than about 70.0 pg/mL, greater than about 80.0 pg/mL, greater than about 90 pg/mL, greater than about 0.1 ng/mL, greater than about 0.2 ng/mL, greater than about 0.3 ng/mL, greater than about 0.4 ng/mL, greater than about 0.5 ng/mL, greater than about 0.6 ng/mL, greater than about 0.7 ng/mL, greater than about 0.8 ng/mL, greater than about 0.9 ng/mL, greater than about 1.0 ng/mL, greater than about 1.5 ng/mL, greater than about 2.0 ng/mL, greater than about 2.5 ng/mL, greater than about 3.0 ng/mL, greater than about 3.5 ng/mL, greater than about 4.0 ng/mL, greater than about 4.5 ng/mL, greater than about 5.0 ng/mL, greater than about 5.5 ng/mL, greater than about 6.0 ng/mL, greater than about 6.5 ng/mL, greater than about 7.0 ng/mL, greater than about 7.5 ng/mL, greater than about 8.0 ng/mL, greater than about 8.5 ng/mL, greater than about 9.0 ng/mL, greater than about 9.5 ng/mL, or greater than about 10.0 ng/mL.

In particular embodiments of the present disclosure, a mean IL-10 serum trough concentration is in the range of from 1.0 pg/mL to 10 ng/mL. In some embodiments, the mean IL-10 serum trough concentration is in the range of from 1.0 pg/mL to 100 pg/mL. In other embodiments, the mean IL-10 serum trough concentration is in the range of from 0.1 ng/mL to 1.0 ng/mL. In still other embodiments, the mean IL-10 serum trough concentration is in the range of from 1.0 ng/mL to 10 ng/mL. It is to be understood that the present disclosure contemplates ranges incorporating any concentrations encompassed by those set forth herein even if such ranges are not explicitly recited. By way of example, the mean serum IL-10 concentration in an embodiment can be in the range of from 0.5 ng/mL to 5 ng/mL. By way of further examples, particular embodiments of the present disclosure comprise a mean IL-10 serum trough concentration in a range of from about 0.5 ng/mL to about 10.5 ng/mL, from about 1.0 ng/mL to about 10.0 ng/mL, from about 1.0 ng/mL to about 9.0 ng/mL, from about 1.0 ng/mL to about 8.0 ng/mL, from about 1.0 ng/mL to about 7.0 ng/mL, from about 1.5 ng/mL to about 10.0 ng/mL, from about 1.5 ng/mL to about 9.0 ng/mL, from about 1.5 ng/mL to about 8.0 ng/mL, from about 1.5 ng/mL to about 7.0 ng/mL, from about 2.0 ng/mL to about 10.0 ng/mL, from about 2.0 ng/mL to about 9.0 ng/mL, from about 2.0 ng/mL to about 8.0 ng/mL, and from about 2.0 ng/mL to about 7.0 ng/mL.

In particular embodiments, a mean IL-10 serum trough concentration of 1-2 ng/mL is maintained over the duration of treatment. The present disclosure also contemplates embodiments wherein the mean IL-10 serum peak concentration is less than or equal to about 10.0 ng/mL over the duration of treatment. Further embodiments contemplate a mean IL-10 serum trough concentration greater than or equal to about 1.0 pg/mL. The optimal mean serum concentration is generally that at which the desired therapeutic effect is achieved without introducing undesired adverse effects.

Certain embodiments of the present disclosure provide a method for monitoring a subject receiving IL-10 therapy to predict, and thus potentially avoid, adverse effects, the method comprising: (1) measuring the subject's peak concentration of IL-10; (2) measuring the subject's trough concentration of IL-10; (3) calculating a peak-trough fluctuation; and, (4) using the calculated peak-trough fluctuation to predict potential adverse effects in the subject. In particular subject populations, a smaller peak-trough fluctuation indicates a lower probability that the subject will experience IL-10-related adverse effects. In addition, in some embodiments particular peak-trough fluctuations are determined for the treatment of particular diseases, disorders and conditions using particular dosing parameters, and those fluctuations are used as reference standards.

For the majority of drugs, plasma drug concentrations decline in a multi-exponential fashion. Immediately after intravenous administration, the drug rapidly distributes throughout an initial space (minimally defined as the plasma volume), and then a slower, equilibrative distribution to extravascular spaces (e.g., certain tissues) occurs. Intravenous IL-10 administration is associated with such a two-compartment kinetic model (see Rachmawati, H. et al. (2004) Pharm. Res. 21(11):2072-78). The pharmacokinetics of subcutaneous recombinant hIL-10 has also been studied (Radwanski, E. et al. (1998) Pharm. Res. 15(12):1895-1901). Thus, volume-of-distribution considerations are pertinent when assessing appropriate IL-10 dosing-related parameters. Moreover, efforts to target IL-10 agents to specific cell types have been explored (see, e.g., Rachmawati, H. (May 2007) Drug Met. Dist. 35(5):814-21), and the leveraging of IL-10 pharmacokinetic and dosing principles can prove invaluable to the success of such efforts.

The present disclosure contemplates administration of any dose and dosing regimen that results in maintenance of any of the IL-10 serum trough concentrations set forth above. By way of example, but not limitation, when the subject is a human, non-pegylated hIL-10 can be administered at a dose greater than 0.5 µg/kg/day, greater than 1.0 µg/kg/day, greater than 2.5 µg/kg/day, greater than 5 µg/kg/day, greater than 7.5 µg/kg, greater than 10.0 µg/kg, greater than 12.5 µg/kg, greater than 15 µg/kg/day, greater than 17.5 µg/kg/day, greater than 20 µg/kg/day, greater than 22.5 µg/kg/day, greater than 25 µg/kg/day, greater than 30 µg/kg/day, or greater than 35 µg/kg/day. In addition, by way of example, but not limitation, when the subject is a human, pegylated hIL-10 comprising a relatively small PEG (e.g., 5 kDa mono-di-PEG-hIL-10) can be administered at a dose greater than 0.5 µg/kg/day, greater than 0.75 µg/kg/day, greater than 1.0 g/kg/day, greater than 1.25 µg/kg/day, greater than 1.5 µg/kg/day, greater than 1.75 µg/kg/day, greater than 2.0 µg/kg/day, greater than 2.25 µg/kg/day, greater than 2.5 µg/kg/day, greater than 2.75 µg/kg/day, greater than 3.0 µg/kg/day, greater than 3.25 µg/kg/day, greater than 3.5 g/kg/day, greater than 3.75 µg/kg/day, greater than 4.0 µg/kg/day, greater than 4.25 µg/kg/day, greater than 4.5 µg/kg/day, greater than 4.75 µg/kg/day, or greater than 5.0 µg/kg/day.

Although the preceding discussion regarding IL-10 serum concentrations, doses and treatment protocols that are necessary to achieve particular IL-10 serum concentrations, etc., pertains to monotherapy with an IL-10 agent (e.g., PEG-IL-10), the skilled artisan (e.g., a pharmacologist) is able to determine the optimum dosing regimen(s) when an IL-10 agent (e.g., PEG-IL-10) is administered in combination with one or more additional therapies.

Methods of Production of IL-10

A polypeptide of the present disclosure can be produced by any suitable method, including non-recombinant (e.g., chemical synthesis) and recombinant methods.

A. Chemical Synthesis

Where a polypeptide is chemically synthesized, the synthesis can proceed via liquid-phase or solid-phase. Solid-phase peptide synthesis (SPPS) allows the incorporation of unnatural amino acids and/or peptide/protein backbone modification. Various forms of SPPS, such as 9-fluorenyl-methoxycarbonyl (Fmoc) and t-butyloxycarbonyl (Boc), are available for synthesizing polypeptides of the present disclosure. Details of the chemical syntheses are known in the art (e.g., Ganesan A. (2006) Mini Rev. Med. Chem. 6:3-10; and Camarero J. A. et al., (2005) Protein Pept Lett. 12:723-8).

Solid phase peptide synthesis can be performed as described hereafter. The alpha functions (Nα) and any reactive side chains are protected with acid-labile or base-labile groups. The protective groups are stable under the conditions for linking amide bonds but can readily be cleaved without impairing the peptide chain that has formed. Suitable protective groups for the α-amino function include, but are not limited to, the following: Boc, benzyloxycarbonyl (Z), O-chlorobenzyloxycarbonyl, bi-phenylisopropyloxycarbonyl, tert-amyloxycarbonyl (Amoc), α, α-dimethyl-3,5-dimethoxy-benzyloxycarbonyl, o-nitrosulfenyl, 2-cyano-t-butoxy-carbonyl, Fmoc, 1-(4,4-dimethyl-2,6-dioxocylohex-1-ylidene)ethyl (Dde) and the like.

Suitable side chain protective groups include, but are not limited to: acetyl, allyl (All), allyloxycarbonyl (Alloc), benzyl (Bzl), benzyloxycarbonyl (Z), t-butyloxycarbonyl (Boc), benzyloxymethyl (Bom), o-bromobenzyloxycarbonyl, t-butyl (tBu), t-butyldimethylsilyl, 2-chlorobenzyl, 2-chlorobenzyloxycarbonyl, 2,6-dichlorobenzyl, cyclohexyl, cyclopentyl, 1-(4,4-dimethyl-2,6-dioxocyclohex-1-ylidene)ethyl (Dde), isopropyl, 4-methoxy-2,3-6-trimethylbenzylsulfonyl (Mtr), 2,3,5,7,8-pentamethylchroman-6-sulfonyl (Pmc), pivalyl, tetrahydropyran-2-yl, tosyl (Tos), 2,4,6-trimethoxybenzyl, trimethylsilyl and trityl (Trt).

In the solid phase synthesis, the C-terminal amino acid is coupled to a suitable support material. Suitable support materials are those which are inert towards the reagents and reaction conditions for the step-wise condensation and cleavage reactions of the synthesis process and which do not dissolve in the reaction media being used. Examples of commercially-available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. When preparation of the peptidic acid is desired, polystyrene (1%)-divinylbenzene or TentaGel® derivatized with 4-benzyloxybenzyl-alcohol (Wang-anchor) or 2-chlorotrityl chloride can be used. In the case of the peptide amide, polystyrene (1%) divinylbenzene or TentaGel® derivatized with 5-(4'-aminomethyl)-3',5'-dimethoxyphenoxy)valeric acid (PAL-anchor) or p-(2,4-dimethoxyphenyl-amino methyl)-phenoxy group (Rink amide anchor) can be used.

The linkage to the polymeric support can be achieved by reacting the C-terminal Fmoc-protected amino acid with the support material by the addition of an activation reagent in ethanol, acetonitrile, N,N-dimethylformamide (DMF), dichloromethane, tetrahydrofuran, N-methylpyrrolidone or similar solvents at room temperature or elevated temperatures (e.g., between 40° C. and 60° C.) and with reaction times of, e.g., 2 to 72 hours.

The coupling of the Na-protected amino acid (e.g., the Fmoc amino acid) to the PAL, Wang or Rink anchor can, for example, be carried out with the aid of coupling reagents such as N,N'-dicyclohexylcarbodiimide (DCC), N,N'-diisopropylcarbodiimide (DIC) or other carbodiimides, 2-(1H-benzotriazol-1-yl)-1,1,3,3-tetramethyluronium tetrafluoroborate (TBTU) or other uronium salts, O-acyl-ureas, benzotriazol-1-yl-tris-pyrrolidino-phosphonium hexafluorophosphate (PyBOP) or other phosphonium salts, N-hydroxysuccinimides, other N-hydroxyimides or oximes in the presence or absence of 1-hydroxybenzotriazole or 1-hydroxy-7-azabenzotriazole, e.g., with the aid of TBTU with addition of HOBt, with or without the addition of a base such as, for example, diisopropylethylamine (DIEA), triethylamine or N-methylmorpholine, e.g., diisopropylethylamine with reaction times of 2 to 72 hours (e.g., 3 hours in a 1.5 to 3-fold excess of the amino acid and the coupling reagents, for example, in a 2-fold excess and at temperatures between about 10° C. and 50° C., for example, 25° C. in a solvent such as dimethylformamide, N-methylpyrrolidone or dichloromethane, e.g., dimethylformamide).

Instead of the coupling reagents, it is also possible to use the active esters (e.g., pentafluorophenyl, p-nitrophenyl or the like), the symmetric anhydride of the Nα-Fmoc-amino acid, its acid chloride or acid fluoride, under the conditions described above.

The Nα-protected amino acid (e.g., the Fmoc amino acid) can be coupled to the 2-chlorotrityl resin in dichloromethane with the addition of DIEA and having reaction times of 10 to 120 minutes, e.g., 20 minutes, but is not limited to the use of this solvent and this base.

The successive coupling of the protected amino acids can be carried out according to conventional methods in peptide synthesis, typically in an automated peptide synthesizer. After cleavage of the Nα-Fmoc protective group of the coupled amino acid on the solid phase by treatment with, e.g., piperidine (10% to 50%) in dimethylformamide for 5 to 20 minutes, e.g., 2×2 minutes with 50% piperidine in DMF and 1×15 minutes with 20% piperidine in DMF, the next protected amino acid in a 3 to 10-fold excess, e.g., in a 10-fold excess, is coupled to the previous amino acid in an inert, non-aqueous, polar solvent such as dichloromethane, DMF or mixtures of the two and at temperatures between about 10° C. and 50° C., e.g., at 25° C. The previously mentioned reagents for coupling the first Nα-Fmoc amino acid to the PAL, Wang or Rink anchor are suitable as coupling reagents. Active esters of the protected amino acid, or chlorides or fluorides or symmetric anhydrides thereof can also be used as an alternative.

At the end of the solid phase synthesis, the peptide is cleaved from the support material while simultaneously cleaving the side chain protecting groups. Cleavage can be carried out with trifluoroacetic acid or other strongly acidic media with addition of 5%-20% V/V of scavengers such as dimethylsulfide, ethylmethylsulfide, thioanisole, thiocresol, m-cresol, anisole ethanedithiol, phenol or water, e.g., 15% v/v dimethylsulfide/ethanedithiol/m-cresol 1:1:1, within 0.5 to 3 hours, e.g., 2 hours. Peptides with fully protected side chains are obtained by cleaving the 2-chlorotrityl anchor with glacial acetic acid/trifluoroethanol/dichloromethane 2:2:6. The protected peptide can be purified by chromatography on silica gel. If the peptide is linked to the solid phase via the Wang anchor and if it is intended to obtain a peptide with a C-terminal alkylamidation, the cleavage can be carried out by aminolysis with an alkylamine or fluoroalkylamine. The aminolysis is carried out at temperatures between about –10° C. and 50° C. (e.g., about 25° C.), and reaction times between about 12 and 24 hours (e.g., about 18 hours). In addition the peptide can be cleaved from the support by re-esterification, e.g., with methanol.

The acidic solution that is obtained can be admixed with a 3 to 20-fold amount of cold ether or n-hexane, e.g., a 10-fold excess of diethyl ether, in order to precipitate the peptide and hence to separate the scavengers and cleaved protective groups that remain in the ether. A further purification can be carried out by re-precipitating the peptide several times from glacial acetic acid. The precipitate that is obtained can be taken up in water or tert-butanol or mixtures of the two solvents, e.g., a 1:1 mixture of tert-butanol/water, and freeze-dried.

The peptide obtained can be purified by various chromatographic methods, including ion exchange over a weakly basic resin in the acetate form; hydrophobic adsorption chromatography on non-derivatized polystyrene/divinylbenzene copolymers (e.g., Amberlite® XAD); adsorption chromatography on silica gel; ion exchange chromatography, e.g., on carboxymethyl cellulose; distribution chromatography, e.g., on Sephadex® G-25; countercurrent distribution chromatography; or high pressure liquid chromatography (HPLC) e.g., reversed-phase HPLC on octyl or octadecylsilylsilica (ODS) phases.

B. Recombinant Production

Methods describing the preparation of human and mouse IL-10 can be found in, for example, U.S. Pat. No. 5,231,012, which teaches methods for the production of proteins having IL-10 activity, including recombinant and other synthetic techniques. IL-10 can be of viral origin, and the cloning and expression of a viral IL-10 from Epstein Barr virus (BCRF1 protein) is disclosed in Moore et al., (1990) Science 248: 1230. IL-10 can be obtained in a number of ways using standard techniques known in the art, such as those described herein. Recombinant human IL-10 is also commercially available, e.g., from PeproTech, Inc., Rocky Hill, N.J.

Where a polypeptide is produced using recombinant techniques, the polypeptide can be produced as an intracellular protein or as a secreted protein, using any suitable construct and any suitable host cell, which can be a prokaryotic or eukaryotic cell, such as a bacterial (e.g., *E. coli*) or a yeast host cell, respectively. Other examples of eukaryotic cells that can be used as host cells include insect cells, mammalian cells, and/or plant cells. Where mammalian host cells are used, they can include human cells (e.g., HeLa, 293, H9 and Jurkat cells); mouse cells (e.g., NIH3T3, L cells, and C127 cells); primate cells (e.g., Cos 1, Cos 7 and CV1); and hamster cells (e.g., Chinese hamster ovary (CHO) cells).

A variety of host-vector systems suitable for the expression of a polypeptide can be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and can provide for inducible or constitutive expression where the coding region is operably-linked under the transcriptional control of the transcriptional initiation region, and a transcriptional and translational termination region. In general, the transcriptional and translational regulatory sequences can include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host can be present to facilitate selection of cells containing the vector. Moreover, the expression construct can include additional elements. For example, the expression vector can have one or two replication systems, thus allowing it to be maintained in organisms, for example, in mammalian or insect cells for expression and in a prokaryotic host for cloning and amplification. In addition, the expression construct can contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification. In one embodiment, the protein can be isolated using metal chelate chromatography methods. Proteins can contain modifications to facilitate isolation.

The polypeptides can be prepared in substantially pure or isolated form (e.g., free from other polypeptides). The polypeptides can be present in a composition that is enriched for the polypeptide relative to other components that can be present (e.g., other polypeptides or other host cell components). For example, purified polypeptide can be provided such that the polypeptide is present in a composition that is substantially free of other expressed proteins, e.g., less than about 90%, less than about 60%, less than about 50%, less than about 40%, less than about 30%, less than about 20%, less than about 10%, less than about 5%, or less than about 1%.

An IL-10 polypeptide can be generated using recombinant techniques to manipulate different IL-10-related nucleic acids known in the art to provide constructs capable of encoding the IL-10 polypeptide. It will be appreciated that, when provided a particular amino acid sequence, the ordinary skilled artisan will recognize a variety of different nucleic acid molecules encoding such amino acid sequence in view of her background and experience in, for example, molecular biology.

Amide Bond Substitutions

In some cases, IL-10 includes one or more linkages other than peptide bonds, e.g., at least two adjacent amino acids are joined via a linkage other than an amide bond. For example, in order to reduce or eliminate undesired proteolysis or other means of degradation, and/or to increase serum stability, and/or to restrict or increase conformational flexibility, one or more amide bonds within the backbone of IL-10 can be substituted.

In another example, one or more amide linkages (—CO—NH—) in IL-10 can be replaced with a linkage which is an isostere of an amide linkage, such as —CH$_2$NH—, —CH$_2$S—, —CH$_2$CH$_2$—, —CH=CH-(cis and trans), —COCH$_2$—, —CH(OH)CH$_2$— or —CH$_2$SO—. One or more amide linkages in IL-10 can also be replaced by, for example, a reduced isostere pseudopeptide bond. See Couder et al. (1993) Int. J. Peptide Protein Res. 41:181-184. Such replacements and how to effect them are known to those of ordinary skill in the art.

Amino Acid Substitutions

One or more amino acid substitutions can be made in an IL-10 polypeptide. The following are non-limiting examples:

a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from C1-C10 carbons including branched, cyclic and straight chain alkyl, alkenyl or alkynyl substitutions;

b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains, including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination), carboxylic acids or any of the many well-known activated derivatives such as acid chlorides, active esters, active azolides and related derivatives, and lysine, ornithine, or 2,3-diaminopropionic acid;

d) substitution of acidic amino acids, including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids;

e) substitution of side chain amide residues, including asparagine, glutamine, and alkyl or aromatic substituted derivatives of asparagine or glutamine; and f) substitution of hydroxyl-containing amino acids, including serine, threonine, homoserine, 2,3-diaminopropionic acid, and alkyl or aromatic substituted derivatives of serine or threonine.

In some cases, IL-10 comprises one or more naturally occurring non-genetically encoded L-amino acids, synthetic L-amino acids, or D-enantiomers of an amino acid. For example, IL-10 can comprise only D-amino acids. For example, an IL-10 polypeptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

Additional Modifications

A cysteine residue or a cysteine analog can be introduced into an IL-10 polypeptide to provide for linkage to another peptide via a disulfide linkage or to provide for cyclization of the IL-10 polypeptide. Methods of introducing a cysteine or cysteine analog are known in the art; see, e.g., U.S. Pat. No. 8,067,532.

An IL-10 polypeptide can be cyclized. One or more cysteines or cysteine analogs can be introduced into an IL-10 polypeptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moieties) that can form a cyclizing bond can be used and/or introduced. A cyclizing bond can be generated with any combination of amino acids (or with an amino acid and —(CH2)$_n$—CO— or —(CH2)$_n$—C$_6$H4-CO—) with functional groups which allow for the introduction of a bridge. Some examples are disulfides, disulfide mimetics such as the —(CH2)$_n$— carba bridge, thioacetal, thioether bridges (cystathionine or lanthionine) and bridges containing esters and ethers. In these examples, n can be any integer, but is frequently less than ten.

Other modifications include, for example, an N-alkyl (or aryl) substitution (ψ[CONR]), or backbone crosslinking to construct lactams and other cyclic structures. Other derivatives include C-terminal hydroxymethyl derivatives, o-modified derivatives (e.g., C-terminal hydroxymethyl benzyl ether), N-terminally modified derivatives including substituted amides such as alkylamides and hydrazides.

In some cases, one or more L-amino acids in an IL-10 polypeptide is replaced with one or more D-amino acids.

In some cases, an IL-10 polypeptide is a retroinverso analog (see, e.g., Sela and Zisman (1997) FASEB J. 11:449). Retro-inverso peptide analogs are isomers of linear polypeptides in which the direction of the amino acid sequence is reversed (retro) and the chirality, D- or L-, of one or more amino acids therein is inverted (inverso), e.g., using D-amino acids rather than L-amino acids. [See, e.g., Jameson et al. (1994) Nature 368:744; and Brady et al. (1994) Nature 368:692].

An IL-10 polypeptide can include a "Protein Transduction Domain" (PTD), which refers to a polypeptide, polynucleotide, carbohydrate, or organic or inorganic molecule that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of an IL-10 polypeptide, while in other embodiments, a PTD is covalently linked to the carboxyl terminus of an IL-10 polypeptide. Exemplary protein transduction domains include, but are not limited to, a minimal undecapeptide protein transduction domain (corresponding to residues 47-57 of HIV-1 TAT comprising YGRKKRRQRRR; SEQ ID NO: 1); a polyarginine sequence comprising a number of arginine residues sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); a *Drosophila* Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:2); Transportan GWTLNSAGYLLGKINLKALAALAKKIL (SEQ ID NO:3);

KALAWEAKLAKALAKALAKHLAKALAKALKCEA (SEQ ID NO:4); and RQIKIWFQNRRMKWKK (SEQ ID NO:5). Exemplary PTDs include, but are not limited to, YGRKKRRQRRR (SEQ ID NO: 1), RKKRRQRRR (SEQ ID NO:6); an arginine homopolymer of from 3 arginine residues to 50 arginine residues; exemplary PTD domain amino acid sequences include, but are not limited to, any of the following: YGRKKRRQRRR (SEQ ID NO: 1); RKKRRQRR (SEQ ID NO:7); YARAAARQARA (SEQ ID NO:8); THRLPRRRRRR (SEQ ID NO:9); and GGRRAR-RRRRR (SEQ ID NO:10).

The carboxyl group $COR_3$ of the amino acid at the C-terminal end of an IL-10 polypeptide can be present in a free form ($R_3$=OH) or in the form of a physiologically-tolerated alkaline or alkaline earth salt such as, e.g., a sodium, potassium or calcium salt. The carboxyl group can also be esterified with primary, secondary or tertiary alcohols such as, e.g., methanol, branched or unbranched C1-C6-alkyl alcohols, e.g., ethyl alcohol or tert-butanol. The carboxyl group can also be amidated with primary or secondary amines such as ammonia, branched or unbranched C1-C6-alkylamines or C1-C6 di-alkylamines, e.g., methylamine or dimethylamine.

The amino group of the amino acid $NR_1R_2$ at the N-terminus of an IL-10 polypeptide can be present in a free form ($R_1$=H and $R_2$=H) or in the form of a physiologically-tolerated salt such as, e.g., a chloride or acetate. The amino group can also be acetylated with acids such that $R_1$=H and $R_2$=acetyl, trifluoroacetyl, or adamantyl. The amino group can be present in a form protected by amino-protecting groups conventionally used in peptide chemistry, such as those provided above (e.g., Fmoc, Benzyloxy-carbonyl (Z), Boc, and Alloc). The amino group can be N-alkylated in which $R_1$ and/or $R_2$=$C_1$-$C_6$ alkyl or $C_2$-$C_8$ alkenyl or $C_7$-$C_9$ aralkyl. Alkyl residues can be straight-chained, branched or cyclic (e.g., ethyl, isopropyl and cyclohexyl, respectively).

Particular Modifications to Enhance and/or Mimic IL-10 Function

It is frequently beneficial, and sometimes imperative, to improve one of more physical properties of the treatment modalities disclosed herein (e.g., IL-10) and/or the manner in which they are administered. Improvements of physical properties include, for example, modulating immunogenicity; methods of increasing water solubility, bioavailability, serum half-life, and/or therapeutic half-life; and/or modulating biological activity. Certain modifications can also be useful to, for example, raise of antibodies for use in detection assays (e.g., epitope tags) and to provide for ease of protein purification. Such improvements must generally be imparted without adversely impacting the bioactivity of the treatment modality and/or increasing its immunogenicity.

Pegylation of IL-10 is one particular modification contemplated by the present disclosure, while other modifications include, but are not limited to, glycosylation (N- and O-linked); polysialylation; albumin fusion molecules comprising serum albumin (e.g., human serum albumin (HSA), cyno serum albumin, or bovine serum albumin (BSA)); albumin binding through, for example a conjugated fatty acid chain (acylation); and Fc-fusion proteins.

Pegylation:

The clinical effectiveness of protein therapeutics is often limited by short plasma half-life and susceptibility to protease degradation. Studies of various therapeutic proteins (e.g., filgrastim) have shown that such difficulties can be overcome by various modifications, including conjugating or linking the polypeptide sequence to any of a variety of nonproteinaceous polymers, e.g., polyethylene glycol (PEG), polypropylene glycol, or polyoxyalkylenes. This is frequently effected by a linking moiety covalently bound to both the protein and the nonproteinaceous polymer, e.g., a PEG. Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

In addition to the beneficial effects of pegylation on pharmacokinetic parameters, pegylation itself can enhance activity. For example, PEG-IL-10 has been shown to be more efficacious against certain cancers than unpegylated IL-10 (see, e.g., EP 206636A2).

PEGs suitable for conjugation to a polypeptide sequence are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in the present disclosure is not restricted to any particular range, and examples are set forth elsewhere herein; by way of example, certain embodiments have molecular weights between 5 kDa and 20 kDa, while other embodiments have molecular weights between 4 kDa and 10 kDa.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. Cation exchange chromatography can be used to separate conjugates, and a fraction is then identified which contains the conjugate having, for example, the desired number of PEGs attached, purified free from unmodified protein sequences and from conjugates having other numbers of PEGs attached.

Pegylation most frequently occurs at the alpha amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies known in the art can be applied herein.

Two widely used first generation activated monomethoxy PEGs (mPEGs) are succinimdyl carbonate PEG (SC-PEG; see, e.g., Zalipsky, et al. (1992) Biotehnol. Appl. Biochem 15:100-114; and Miron and Wilcheck (1993) Bio-conjug. Chem. 4:568-569) and benzotriazole carbonate PEG (BTC-PEG; see, e.g., Dolence, et al. U.S. Pat. No. 5,650,234), which react preferentially with lysine residues to form a carbamate linkage, but are also known to react with histidine and tyrosine residues. The linkage to histidine residues on certain molecules (e.g., IFNα) has been shown to be a hydrolytically unstable imidazolecarbamate linkage (see, e.g., Lee and McNemar, U.S. Pat. No. 5,985,263). Second generation pegylation technology has been designed to avoid these unstable linkages as well as the lack of selectivity in residue reactivity. Use of a PEG-aldehyde linker targets a single site on the N-terminus of a polypeptide through reductive amination.

PEG can be bound to a polypeptide of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide. Another activated polyethylene glycol which can be bound to a free amino group is 2,4-bis(O-methoxypolyethyleneglycol)-6-chloro-s-triazine, which can be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer can be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions can be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art can be used to terminate the reaction. In some embodiments the reaction is terminated by acidifying the reaction mixture and freezing at, e.g., −20° C. Pegylation of various molecules is discussed in, for example, U.S. Pat. Nos. 5,252,714; 5,643,575; 5,919,455; 5,932,462; and 5,985,263. PEG-IL-10 is described in, e.g., U.S. Pat. No. 7,052,686. Specific reaction conditions contemplated for use herein are set forth in the Experimental section.

The present disclosure also contemplates the use of PEG mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix's XTEN technology; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

Glycosylation:

For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present.

Glycosylation can dramatically affect the physical properties (e.g., solubility) of polypeptides such as IL-10 and can also be important in protein stability, secretion, and subcellular localization. Glycosylated polypeptides can also exhibit enhanced stability or can improve one or more pharmacokinetic properties, such as half-life. In addition, solubility improvements can, for example, enable the generation of formulations more suitable for pharmaceutical administration than formulations comprising the non-glycosylated polypeptide.

Addition of glycosylation sites can be accomplished by altering the amino acid sequence. The alteration to the polypeptide can be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type can be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, can confer acidic properties to the glycoprotein. A particular embodiment of the present disclosure comprises the generation and use of N-glycosylation variants.

The polypeptide sequences of the present disclosure can optionally be altered through changes at the nucleic acid level, particularly by mutating the nucleic acid encoding the polypeptide at preselected bases such that codons are generated that will translate into the desired amino acids.

Polysialylation:

The present disclosure also contemplates the use of polysialylation, the conjugation of polypeptides to the naturally occurring, biodegradable α-(2→8) linked polysialic acid ("PSA") in order to improve the polypeptides' stability and in vivo pharmacokinetics. PSA is a biodegradable, non-toxic natural polymer that is highly hydrophilic, giving it a high apparent molecular weight in the blood which increases its serum half-life. In addition, polysialylation of a range of peptide and protein therapeutics has led to markedly reduced proteolysis, retention of activity in vivo activity, and reduction in immunogenicity and antigenicity (see, e.g., G. Gregoriadis et al., Int. J. Pharmaceutics 300(1-2):125-30). Various techniques for site-specific polysialylation are available (see, e.g., T. Lindhout et al., PNAS 108(18)7397-7402 (2011)).

Albumin Fusion:

Additional suitable components and molecules for conjugation include albumins such as human serum albumin (HSA), cyno serum albumin, and bovine serum albumin (BSA).

According to the present disclosure, albumin can be conjugated to a drug molecule (e.g., a polypeptide described herein) at the carboxyl terminus, the amino terminus, both the carboxyl and amino termini, and internally (see, e.g., U.S. Pat. No. 5,876,969 and U.S. Pat. No. 7,056,701).

In the HSA-drug molecule conjugates contemplated by the present disclosure, various forms of albumin can be used, such as albumin secretion pre-sequences and variants thereof, fragments and variants thereof, and HSA variants. Such forms generally possess one or more desired albumin activities. In additional embodiments, the present disclosure involves fusion proteins comprising a polypeptide drug molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker, such as a peptide linker or modified version thereof.

As alluded to above, fusion of albumin to one or more polypeptides of the present disclosure can, for example, be achieved by genetic manipulation, such that the nucleic acid coding for HSA, or a fragment thereof, is joined to the nucleic acid coding for the one or more polypeptide sequences.

Alternative Albumin Binding Strategies:

Several albumin-binding strategies have been developed as alternatives to direct fusion and can be used with the IL-10 agents described herein. By way of example, the present disclosure contemplates albumin binding through a conjugated fatty acid chain (acylation) and fusion proteins which comprise an albumin binding domain (ABD) polypeptide sequence and the sequence of one or more of the polypeptides described herein.

Conjugation with Other Molecules:

Additional suitable components and molecules for conjugation include, for example, thyroglobulin; tetanus toxoid; Diphtheria toxoid; polyamino acids such as poly(D-lysine: D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing.

Thus, the present disclosure contemplates conjugation of one or more additional components or molecules at the N- and/or C-terminus of a polypeptide sequence, such as another polypeptide (e.g., a polypeptide having an amino acid sequence heterologous to the subject polypeptide), or a carrier molecule. Thus, an exemplary polypeptide sequence can be provided as a conjugate with another component or molecule.

An IL-10 polypeptide can also be conjugated to large, slowly metabolized macromolecules such as proteins; polysaccharides, such as sepharose, agarose, cellulose, or cellulose beads; polymeric amino acids such as polyglutamic acid, or polylysine; amino acid copolymers; inactivated virus particles; inactivated bacterial toxins such as toxoid from diphtheria, tetanus, cholera, or leukotoxin molecules; inactivated bacteria; and dendritic cells. Such conjugated forms can, if desired, be used to produce antibodies against a polypeptide of the present disclosure.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Fc-Fusion Molecules:

In certain embodiments, the amino- or carboxyl-terminus of a polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product can require less frequent administration.

Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

Other Modifications:

The present disclosure contemplates the use of other modifications, currently known or developed in the future, of IL-10 to improve one or more properties. Examples include hesylation, various aspects of which are described in, for example, U.S. Patent Appln. Nos. 2007/0134197 and 2006/0258607, and fusion molecules comprising SUMO as a fusion tag (LifeSensors, Inc.; Malvern, Pa.).

Linkers:

Linkers and their use have been described above. Any of the foregoing components and molecules used to modify the polypeptide sequences of the present disclosure may optionally be conjugated via a linker. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids.

Examples of flexible linkers include glycine polymers $(G)_n$, glycine-alanine polymers, alanine-serine polymers, glycine-serine polymers (for example, (GmSo)n, $(GSGGS)_n$ (SEQ ID NO: 11), $(G_mS_oG_m)_n$, $(G_mS_oG_mS_oG_m)_n$ (SEQ ID NO: 12), $(GSGGS_m)_n$ (SEQ ID NO: 11), $(GSGS_mG)_n$ (SEQ ID NO: 12) and $(GGGS_m)_n$ (SEQ ID NO: 13), and combinations thereof, where m, n, and o are each independently selected from an integer of at least 1 to 20, e.g., 1-18, 2-16, 3-14, 4-12, 5-10, 1, 2, 3, 4, 5, 6, 7, 8, 9, or 10), and other flexible linkers. Glycine and glycine-serine polymers are relatively unstructured, and therefore may serve as a neutral tether between components. Examples of flexible linkers include, but are not limited to GGSG (SEQ ID NO:14), GGSGG (SEQ ID NO: 15), GSGSG (SEQ ID NO: 12), GSGGG (SEQ ID NO: 16), GGGSG (SEQ ID NO:17), and GSSSG (SEQ ID NO:18).

Additional examples of flexible linkers include glycine polymers $(G)_n$ or glycine-serine polymers (e.g., $(GS)_n$, $(GSGGS)_n$ (SEQ ID NO: 11), $(GGGS)_n$ (SEQ ID NO: 13) and $(GGGGS)_n$ (SEQ ID NO: 19), where n=1 to 50, for example, 1, 2, 3, 4, 5, 6, 7, 8, 9, 10, 10-20, 20-30, 30-50). Exemplary flexible linkers include, but are not limited to GGGS (SEQ ID NO: 13), GGGGS (SEQ ID NO:19), GGSG (SEQ ID NO:14), GGSGG (SEQ ID NO:15), GSGSG (SEQ ID NO:12), GSGGG (SEQ ID NO:16), GGGSG (SEQ ID NO:17), and GSSSG (SEQ ID NO:18). A multimer (e.g., 1, 2, 3, 4, 5, 6, 7, 8, 9, 10, 10-20, 20-30, or 30-50) of these linker sequences may be linked together to provide flexible linkers that may be used to conjugate a heterologous amino acid sequence to the IL-10 agents disclosed herein. As described herein, the heterologous amino acid sequence may be a signal sequence and/or a fusion partner, such as, albumin, Fc sequence, and the like.

Therapeutic and Prophylactic Uses

The present disclosure contemplates the use of the IL-10 agents described herein (e.g., PEG-IL-10) to prevent or reduce the severity of activation-induced cell death in patients undergoing CAR-T cell therapy. More specifically, IL-10 agents are used in methods directed to the modulation of a T cell-mediated immune response to a target cell population in a subject, comprising introducing to the subject a therapeutically effective plurality of cells genetically modified to express a chimeric antigen receptor, wherein the chimeric antigen receptor comprises at least one antigen-specific targeting region capable of binding to the target cell population, and wherein the binding of the chimeric antigen receptor targeting region to the target cell population is capable of eliciting activation-induced cell death.

In particular embodiments, a therapeutically effective amount of the IL-10 agent sufficient to prevent or limit the activation-induced cell death is administered parenterally (e.g., subcutaneously) to the subject. In other embodiments, a therapeutically effective plurality of cells genetically modified to express a chimeric antigen receptor and an IL-10 agent in an amount sufficient to prevent or limit the activation-induced cell death is introduced into the subject. In still further embodiments, a therapeutically effective amount of the IL-10 agent sufficient to prevent or limit the activation-induced cell death is introduced into the subject by means of cells genetically modified to express the IL-10 agent, whereby the expression construct is present in different cells than those that express a CAR.

The genetic material encoding an IL-10 agent can be introduced into cells by any means known to the skilled artisan. The two major classes of methods are those that use recombinant viruses (also referred to as viral vectors) and those that use naked DNA or DNA complexes (non-viral methods). Examples of viruses that may be used include, but are not limited to, retroviruses, adenoviruses and herpes simplex virus. Examples of non-viral methods include, but are not limited to, injection of naked DNA, physical methods to enhance delivery (e.g., electroporation), and chemical methods to enhance delivery (e.g., lipoplexes).

In certain embodiments of the present disclosure, a vector (e.g., a viral vector) is genetically engineered to deliver the gene. The vector can be given intravenously or injected directly into a specific tissue in the body, where it is taken up by individual cells. Alternately, a portion of the subject's cells can be removed and exposed to the vector in an ex vivo setting, followed by the return of the cells containing the vector to the patient. In particular embodiments, expression of the IL-10 agent is modulated by an expression control element.

The CAR-T cell therapy used in conjunction with an IL-10 agent described herein can be used to treat or prevent a proliferative disease, disorder or condition, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present disclosure also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The disclosure contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In other embodiments, the CAR-T cell therapy used in conjunction with an IL-10 agent described herein can be used to treat or prevent an immune/inflammatory-related disorder. As used herein, terms such as "immune disease", "immune condition", "immune disorder", "inflammatory disease", "inflammatory condition", "inflammatory disorder" and the like are meant to broadly encompass any immune- or inflammatory-related condition (e.g., pathological inflammation and autoimmune diseases). Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

A non-limiting list of immune- and inflammatory-related diseases, disorders and conditions includes arthritis (e.g., rheumatoid arthritis), kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), allergic contact dermatitis and other eczemas, systemic sclerosis, transplantation and multiple sclerosis.

Pharmaceutical Compositions

When an IL-10 agent is administered to a subject, the present disclosure contemplates the use of any form of compositions suitable for administration to the subject. In general, such compositions are "pharmaceutical compositions" comprising IL-10 and one or more pharmaceutically acceptable or physiologically acceptable diluents, carriers or excipients. The pharmaceutical compositions can be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein. Furthermore, the pharmaceutical compositions can be used in combination with other therapeutically active agents or compounds as described herein in order to treat or prevent the diseases, disorders and conditions as contemplated by the present disclosure.

The pharmaceutical compositions typically comprise a therapeutically effective amount of an IL-10 agent contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle can be a physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it can be stored in sterile vials as a solution, suspension, gel, emulsion, solid, or dehydrated or lyophilized powder. Such formulations can be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus can be used to deliver IL-10, including implants (e.g., implantable pumps) and catheter systems, slow injection pumps and devices, all of which are well known to the skilled artisan. Depot injections, which are generally administered subcutaneously or intramuscularly, can also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions can be in the form of a sterile injectable aqueous or oleagenous suspension. This suspension can be formulated according to the known art using those suitable dispersing or wetting agents and suspending agents mentioned herein. The sterile injectable preparation can also be a sterile injectable solution or suspension in a non-toxic parenterally-acceptable diluent or solvent, for example, as a solution in 1,3-butane diol. Acceptable diluents, solvents and dispersion media that can be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil can be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The pharmaceutical compositions containing the active ingredient can be in a form suitable for oral use, for example, as tablets, capsules, troches, lozenges, aqueous or oily suspensions, dispersible powders or granules, emulsions, hard or soft capsules, or syrups, solutions, microbeads or elixirs. In particular embodiments, an active ingredient of an agent co-administered with an IL-10 agent described herein is in a form suitable for oral use. Pharmaceutical compositions intended for oral use can be prepared according to any method known to the art for the manufacture of pharmaceutical compositions, and such compositions can contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients can be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration can be uncoated or coated by known techniques to delay disintegration and absorption in the gastrointestinal tract and thereby provide a sustained action. For example, a time-delay material such as glyceryl monostearate or glyceryl distearate can be employed. They can also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use can also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxy-ethylene sorbitol monooleate), or condensation products of ethylene oxide with partial esters derived from fatty acids and hexitol anhydrides (e.g., polyethylene sorbitan monooleate). The aqueous suspensions can also contain one or more preservatives.

Oily suspensions can be formulated by suspending the active ingredient in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure can also be in the form of oil-in-water emulsions. The oily phase can be a vegetable oil, for example olive oil or arachis oil, or a mineral oil, for example, liquid paraffin, or mixtures of these. Suitable emulsifying agents can be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, can be employed.

The present disclosure contemplates the administration of the IL-10 polypeptides in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The IL-10 agents (e.g., PEG-IL-10) and other agents contemplated by the present disclosure can be in the form of any other suitable pharmaceutical composition (e.g., sprays for nasal or inhalation use) currently known or developed in the future.

The concentration of a polypeptide (e.g., IL-10) or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present disclosure contemplates the administration of the IL-10 agent (e.g., PEG-IL-10), and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation. Depot injections, which are generally administered subcutaneously or intramuscularly, can also be utilized to release the IL-10 agents disclosed herein over a defined period of time.

In some particular embodiments of the present disclosure, the IL-10 agents (e.g., PEG-IL-10) are administered parenterally, and in further particular embodiments the parenteral administration is subcutaneous.

As to the CAR-T cell therapy, described herein are alternative means for introducing to a subject a therapeutically effective plurality of cells genetically modified to express a chimeric antigen receptor, wherein the chimeric antigen receptor comprises at least one antigen-specific targeting region capable of binding to the target cell population, and wherein the binding of the chimeric antigen receptor targeting region to the target cell population is capable of eliciting activation-induced cell death.

Combination Therapy

In conjunction with the CAR-T T cell therapy described herein, the present disclosure contemplates the use of an IL-10 agent (e.g., PEG-IL-10) in combination with one or more active agents (e.g., chemotherapeutic agents) or other prophylactic or therapeutic non-pharmacological modalities (e.g., localized radiation therapy or total body radiation therapy). By way of example, the present disclosure contemplates treatment regimens wherein a radiation phase is preceded or followed by treatment with one or more additional therapies (e.g., CAR-T T cell therapy and administration of an IL-10 agent) or agents as described herein. In some embodiments, the present disclosure further contemplates the use of CAR-T T cell therapy and an IL-10 agent (e.g., PEG-IL-10) in combination with bone marrow transplantation, peripheral blood stem cell transplantation, or other types of transplantation therapy.

As used herein, "combination therapy" is meant to include therapies that can be administered or introduced separately, for example, formulated separately for separate administration (e.g., as may be provided in a kit), and therapies that can be administered or introduced together. In certain embodiments, the IL-10 agent and the other agent(s) are administered or applied sequentially, e.g., where one agent is administered prior to one or more other agents. In other embodiments, the IL-10 agent and the other agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

The IL-10 agents of the present disclosure may be used in combination with at least one other active agent in any manner appropriate under the circumstances. In one embodiment, treatment with the IL-10 agent and the other agent(s) is maintained over a period of time. In another embodiment, treatment with the at least one other agent(s) is reduced or discontinued (e.g., when the subject is stable), while treatment with an IL-10 agent of the present disclosure (e.g., PEG-IL-10) is maintained at a constant dosing regimen. In a further embodiment, treatment with the other agent(s) is reduced or discontinued (e.g., when the subject is stable), while treatment with an IL-10 agent of the present disclosure is reduced (e.g., lower dose, less frequent dosing or shorter treatment regimen). In yet another embodiment, treatment with the other agent(s) is reduced or discontinued (e.g., when the subject is stable), and treatment with the IL-10 agent of the present disclosure is increased (e.g., higher dose, more frequent dosing or longer treatment regimen). In yet another embodiment, treatment with the other agent(s) is maintained and treatment with the IL-10 agent of the present disclosure is reduced or discontinued (e.g., lower dose, less frequent dosing or shorter treatment regimen). In yet another embodiment, treatment with the other agent(s) and treatment with an IL-10 agent of the present disclosure (e.g., PEG-IL-10) are reduced or discontinued (e.g., lower dose, less frequent dosing or shorter treatment regimen).

In conjunction with the CAR-T T cell therapy described herein, the present disclosure provides methods for treating and/or preventing a proliferative condition, cancer, tumor, or precancerous disease, disorder or condition with an IL-10 agent (e.g., PEG-IL-10) and at least one additional therapeutic or prophylactic agent(s) or diagnostic agent exhibiting a desired activity. Some embodiments of the present disclosure contemplate the use of traditional chemotherapeutic agents (e.g., alkylating agents, nitrogen mustards, nitrosureas, antibiotics, anti-metabolites, folic acid analogs, purine analogs, pyrimidine analogs, antihormonal agents and taxoids). Other embodiments of the present disclosure contemplate methods for tumor suppression or tumor growth comprising administration of an IL-10 agent described herein in combination with a signal transduction inhibitor (e.g., GLEEVEC or HERCEPTIN) or an immunomodulator to achieve additive or synergistic suppression of tumor growth.

In conjunction with the CAR-T T cell therapy described herein, the present disclosure also provides methods for treating and/or preventing immune- and/or inflammatory-related diseases, disorders and conditions, as well as disorders associated therewith, with an IL-10 agent (e.g., PEG-IL-10) and at least one additional agent(s) or diagnostic agent exhibiting a desired activity. Examples of therapeutic agents useful in combination therapy include, but are not limited to non-steroidal anti-inflammatory drugs (NSAIDs), cyclooxygenase-2 (COX-2) inhibitors, steroids, TNF antagonists (e.g., REMICADE and ENBREL), interferon-β1a (AVONEX), interferon-β1b (BETASERON), and immune checkpoint inhibitors (e.g., YERVOY).

Dosing

The IL-10 agents (e.g., PEG-IL-10) of the present disclosure can be administered to a subject in an amount that is dependent upon, for example, the goal of the administration (e.g., the degree of resolution desired); the age, weight, sex, and health and physical condition of the subject the formulation being administered; and the route of administration. Effective dosage amounts and dosage regimens can readily be determined from, for example, safety and dose-escalation trials, in vivo studies (e.g., animal models), and other methods known to the skilled artisan.

As discussed in detail elsewhere, the present disclosure contemplates embodiments wherein administration of IL-10 to achieve certain serum trough concentrations and/or maintain certain mean serum trough concentrations.

In general, dosing parameters dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount can be more than the calculated ED50, in other situations the effective amount can be less than the calculated ED50, and in still other situations the effective amount can be the same as the calculated ED50.

The therapeutically effective amount of PEG-IL-10 can range from about 0.01 to about 100 µg protein/kg of body weight/day, from about 0.1 to 20 µg protein/kg of body weight/day, from about 0.5 to 10 µg protein/kg of body weight/day, or about 1 to 4 µg protein/kg of body weight/day. In some embodiments, PEG-IL-10 is administered by continuous infusion to delivery about 50 to 800 µg protein/kg of body weight/day (e.g., about 1 to 16 µg protein/kg of body weight/day of PEG-IL-10). The infusion rate can be varied based on evaluation of, for example, adverse effects and blood cell counts. Other specific dosing parameters for the IL-10 agents are described elsewhere herein.

In certain embodiments, the dosage of the disclosed IL-10 agent is contained in a "unit dosage form". The phrase "unit dosage form" refers to physically discrete units, each unit containing a predetermined amount of the IL-10 agent of the present disclosure, either alone or in combination with one or more additional agents, sufficient to produce the desired effect. It will be appreciated that the parameters of a unit dosage form will depend on the particular agent and the effect to be achieved.

Kits

The present disclosure also contemplates kits comprising an IL-10 agent (e.g., PEG-IL-10), and a pharmaceutical composition thereof. The kits are generally in the form of a physical structure housing various components, as described below, and can be utilized, for example, in practicing the methods described above.

A kit can include an IL-10 agent (e.g., PEG-IL-10) disclosed herein (provided in, e.g., a sterile container), which can be in the form of a pharmaceutical composition suitable for administration to a subject. The IL-10 agent can be provided in a form that is ready for use or in a form requiring, for example, reconstitution or dilution prior to administration. When the IL-10 agent is in a form that needs to be reconstituted by a user, the kit can also include buffers, pharmaceutically acceptable excipients, and the like, packaged with or separately from the IL-10 agent. A kit can also contain both the IL-10 agent and/or components of the specific CAR-T T cell therapy to be used; the kit can contain the several agents separately or they can already be combined in the kit. A kit of the present disclosure can be designed for conditions necessary to properly maintain the components housed therein (e.g., refrigeration or freezing).

A kit can contain a label or packaging insert including identifying information for the components therein and instructions for their use (e.g., dosing parameters, clinical pharmacology of the active ingredient(s), including mechanism(s) of action, pharmacokinetics and pharmacodynamics, adverse effects, contraindications, etc.). Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via an internet site, are provided.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below were performed and are all of the experiments that can be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: s or sec=second(s); min=minute(s); h or hr=hour(s); aa=amino acid(s); bp=base pair(s); kb=kilobase(s); nt=nucleotide(s); ng=nanogram; µg=microgram; mg=milligram; g=gram; kg=kilogram; dl or dL=deciliter; µl or µL=microliter; ml or mL=milliliter; l or L=liter; nM=nanomolar; µM=micromolar; mM=millimolar; M=molar; kDa=kilodalton; i.m.=intramuscular(ly); i.p.=intraperitoneal(ly); SC or SQ=subcutaneous(ly); HPLC=high performance liquid chromatography; BW=body weight; U=unit; ns=not statistically significant; PMA=Phorbol 12-myristate 13-acetate; PBS=phosphate-buffered saline; DMEM=Dulbeco's Modification of Eagle's Medium; PBMCs=primary peripheral blood mononuclear cells; FBS=fetal bovine serum; FCS=fetal calf serum; HEPES=4-(2-hydroxyethyl)-1-piperazineethanesulfonic acid; LPS=lipopolysaccharide; RPMI=Roswell Park Memorial Institute medium; APC=antigen presenting cells; FACS=fluorescence-activated cell sorting.

Materials and Methods.

The following general materials and methods were used, where indicated, or may be used in the Examples below:

Molecular Biology Procedures.

Standard methods in molecular biology are described in the scientific literature (see, e.g., Sambrook and Russell (2001) Molecular Cloning, 3$^{rd}$ ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

Antibody-Related Processes.

Production, purification, and fragmentation of polyclonal and monoclonal antibodies are described (e.g., Harlow and Lane (1999) Using Antibodies, Cold Spring Harbor Laboratory Press, Cold Spring Harbor, N.Y.); standard techniques for characterizing ligand/receptor interactions are available (see, e.g., Coligan et al. (2001) Current Protocols in Immunology, Vol. 4, John Wiley, Inc., NY); methods for flow cytometry, including fluorescence-activated cell sorting (FACS), are available (see, e.g., Shapiro (2003) Practical Flow Cytometry, John Wiley and Sons, Hoboken, N.J.); and fluorescent reagents suitable for modifying nucleic acids, including nucleic acid primers and probes, polypeptides, and antibodies, for use, e.g., as diagnostic reagents, are available (Molecular Probes (2003) Catalogue, Molecular Probes, Inc., Eugene, Oreg.; Sigma-Aldrich (2003) Catalogue, St. Louis, Mo.). Further discussion of antibodies appears elsewhere herein.

Software.

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, Calif.); and DeCypher™ (TimeLogic Corp., Crystal Bay, Nev.).

Pegylation.

Pegylated IL-10 as described herein may be synthesized by any means known to the skilled artisan. Exemplary synthetic schemes for producing mono-PEG-IL-10 and a mix of mono-/di-PEG-IL-10 have been described (see, e.g., U.S. Pat. No. 7,052,686; US Pat. Publn. No. 2011/0250163; WO 2010/077853). Particular embodiments of the present disclosure comprise a mix of selectively pegylated mono- and di-PEG-IL-10. In addition to leveraging her own skills in the production and use of PEGs (and other drug delivery technologies) suitable in the practice of the present disclosure, the skilled artisan is familiar with many commercial suppliers of PEG-related technologies (e.g., NOF America Corp (Irvine, Calif.) and Parchem (New Rochelle, N.Y.)).

Animals.

Various mice and other animal strains known to the skilled artisan can be used in conjunction with the teachings of the present disclosure. For example, immunocompetent Balb/C or B-cell-deficient Balb/C mice can be obtained from The Jackson Lab., Bar Harbor, Me. and used in accordance with standard procedures (see, e.g., Martin et al (2001) Infect. Immun., 69(11):7067-73 and Compton et al. (2004) Comp. Med. 54(6):681-89).

IL-10 Concentrations.

Serum IL-10 concentration levels and exposure levels can be determined by standard methods used in the art. For example, when the experimental subject is a mouse, a serum exposure level assay can be performed by collecting whole blood (~50 µL/mouse) from mouse tail snips into plain capillary tubes, separating serum and blood cells by centrifugation, and determining IL-10 exposure levels by standard ELISA kits and techniques.

FACS Analysis.

Numerous protocols, materials and reagents for FACS analysis are commercially available and may be used in conjunction with the teachings herein (e.g., Becton-Dickinson, Franklin Lakes, N.J.; Cell Signaling Technologies, Danford, Mass.; Abcam, Cambridge, Mass.; Affymetrix, Santa Clara, Calif.). Both direct flow cytometry (i.e., using a conjugated primary antibody) and indirect flow cytometry (i.e., using a primary antibody and conjugated secondary antibody) may be used. An exemplary direct flow protocol is as follows: Wash harvested cells and adjust cell suspension to a concentration of $1-5 \times 10^6$ cells/mL in ice-cold PBS, 10% FCS, 1% sodium azide. Cells may be stained in polystyrene round bottom $12 \times 75$ mm$^2$ Falcon tubes. Cells may be centrifuged sufficiently so the supernatant fluid may be removed with little loss of cells, but not to the extent that the cells are difficult to resuspend. The primary labeled antibody may be added (0.1-10 µg/mL), and dilutions, if necessary, may be made in 3% BSA/PBS. After incubation for at least 30 min at 4° C., cells may be washed 3× by centrifugation at 400 g for 5 min and then may be resuspended in 0.5-1 mL of ice-cold PBS, 10% FCS, 1% sodium azide. Cells may be maintained in the dark on ice until analysis (preferably within the same day). Cells may also be fixed, using standard methodologies, to preserve them for several days; fixation for different antigens may require antigen-specific optimization.

The assays described hereafter are representative, and not exclusionary.

PBMC and CD8+ T-Cell Gene Expression Assay.

The following protocol provides an exemplary assay to examine gene expression.

Human PBMCs can be isolated according to any standard protocol (see, e.g., Fuss et al. (2009) Current Protocols in Immunology, Unit 7.1, John Wiley, Inc., NY). 2.5 mL of PBMCs (at a cell density of 8 million cells/mL) can be cultured per well with complete RPMI, containing RPMI (Life Technologies; Carlsbad, Calif.), 10 mM HEPES (Life Technologies; Carlsbad, Calif.), 10% FCS (Hyclone Thermo Fisher Scientific; Waltham, Mass.) and Penicillin/Streptomycin cocktail (Life Technologies; Carlsbad, Calif.), in any standard tissue culture treated 6-well plate (BD; Franklin Lakes, N.J.). Human pegylated-IL-10 can be added to the wells at a final concentration of 100 ng/mL, followed by a 7-day incubation. CD8+ T-cells can be isolated from the PBMCs using Miltenyi Biotec's MACS cell separation technology according to the manufacturer's protocol (Miltenyi Biotec; Auburn, Calif.). RNA can be extracted and cDNA can be synthesized from the isolated CD8+ T-cells and the CD8+ T-cell depleted-PBMCs using Qiagen's RNeasy Kit and RT$^2$ First Strand Kit, respectively, following the manufacturer's instructions (Qiagen N.V.; Netherlands). Quantitative PCR can be performed on the cDNA template using the RT$^2$ SYBR Green qPCR Mastermix and primers (IDO1, GUSB, and GAPDH) from Qiagen according to the manufacturer's protocol. IDO1 Ct values can be normalized to the average Ct value of the housekeeping genes, GUSB and GAPDH.

PBMC and CD8+ T-Cell Cytokine Secretion Assay.

Activated primary human CD8+ T-cells secrete IFN-γ when treated with PEG-IL-10 and then with an anti-CD3 antibody. The following protocol provides an exemplary assay to examine cytokine secretion.

Human PBMCs can be isolated according to any standard protocol (see, e.g., Fuss et al. (2009) Current Protocols in Immunology, Unit 7.1, John Wiley, Inc., NY). 2.5 mL of PBMCs (at a cell density of 8 million cells/mL) can be cultured per well with complete RPMI, containing RPMI (Life Technologies; Carlsbad, Calif.), 10 mM HEPES (Life Technologies; Carlsbad, Calif.), 10% FCS (Hyclone Thermo Fisher Scientific; Waltham, Mass.) and Penicillin/Streptomycin cocktail (Life Technologies; Carlsbad, Calif.), in any standard tissue culture treated 6-well plate (BD; Franklin Lakes, N.J.). Human pegylated-IL-10 can be added to the wells at a final concentration of 100 ng/mL, followed by a 3-day incubation. CD8+ T-cells can be isolated from the PBMCs using Miltenyi Biotec's MACS cell separation technology according to the manufacture's protocol (Miltenyi Biotec; Auburn, Calif.). The isolated CD8+ T-cells can then be cultured with complete RPMI containing 1 µg/mL anti-CD3 antibody (Affymetrix eBioscience) in any standard tissue culture plate for 4 hours. After the 4-hour incubation, the media can be collected and assayed for IFN-γ using a commercial ELISA kit and following the manufacture's protocol (Affymetrix eBioscience).

TNFα Inhibition Assay.

PMA-stimulation of U937 cells (lymphoblast human cell line from lung available from Sigma-Aldrich (#85011440); St. Louis, Mo.) causes the cells to secrete TNFα, and subsequent treatment of these TNFα-secreting cells with human IL-10 causes a decrease in TNFα secretion in a dose-dependent manner. An exemplary TNFα inhibition assay can be performed using the following protocol.

After culturing U937 cells in RMPI containing 10% FBS/FCS and antibiotics, plate 1×105, 90% viable U937 cells in 96-well flat bottom plates (any plasma-treated tissue culture plates (e.g., Nunc; Thermo Scientific, USA) can be used) in triplicate per condition. Plate cells to provide for the following conditions (all in at least triplicate; for 'media alone' the number of wells is doubled because one-half will be used for viability after incubation with 10 nM PMA): 5 ng/mL LPS alone; 5 ng/mL LPS+0.1 ng/mL rhIL-10; 5 ng/mL LPS+1 ng/mL rhIL-10; 5 ng/mL LPS+10 ng/mL rhIL-10; 5 ng/mL LPS+100 ng/mL rhIL-10; 5 ng/mL LPS+1000 ng/mL rhIL-10; 5 ng/mL LPS+0.1 ng/mL PEG-rhIL-10; 5 ng/mL LPS+1 ng/mL PEG-rhIL-10; 5 ng/mL LPS+10 ng/mL PEG-rhIL-10; 5 ng/mL LPS+100 ng/mL PEG-rhIL-10; and 5 ng/mL LPS+1000 ng/mL PEG-rhIL-10. Expose each well to 10 nM PMA in 200 µL for 24 hours, culturing at 37° C. in 5% CO$_2$ incubator, after which time ~90% of cells should be adherent. The three extra wells can be re-suspended, and the cells are counted to assess viability (>90% should be viable). Wash gently but thoroughly 3× with fresh, non-PMA-containing media, ensuring that cells are still in the wells. Add 100 µL per well of media containing the appropriate concentrations (2× as the volume will be diluted by 100%) of rhIL-10 or PEG-rhIL-10, incubate at 37° C. in a 5% CO$_2$ incubator for 30 minutes. Add 100 µL per well of 10 ng/mL stock LPS to achieve a final concentration of 5 ng/mL LPS in each well, and incubate at 37° C. in a 5% CO$_2$ incubator for 18-24 hours. Remove supernatant and perform TNFα ELISA according to the manufacturer's instructions. Run each conditioned supernatant in duplicate in ELISA.

MC/9 Cell Proliferation Assay.

IL-10 administration to MC/9 cells (murine cell line with characteristics of mast cells available from Cell Signaling Technology; Danvers, Mass.) causes increased cell proliferation in a dose-dependent manner. Thompson-Snipes, L. et al. (1991) J. Exp. Med. 173:507-10) describe a standard assay protocol in which MC/9 cells are supplemented with IL3+IL-10 and IL-3+IL-4+IL-10. Vendors (e.g., R&D Systems, USA; and Cell Signaling Technology, Danvers, Mass.) use the assay as a lot release assay for rhIL-10. Those of ordinary skill in the art will be able to modify the standard assay protocol described in Thompson-Snipes, L. et al, such that cells are only supplemented with IL-10.

Activation-Induced Cell Death Assay.

The following protocol provides an exemplary activation-induced cell death assay.

Human PBMCs can be isolated according to any standard protocol (see, e.g., Fuss et al. (2009) Current Protocols in Immunology, Unit 7.1, John Wiley, Inc., NY). CD8+ T cells (CD45RO+) can be isolated using Miltenyi Biotec's anti-CD45RO MACS beads and MACS cell separation technology according to the manufacture's protocol (Miltenyi Biotec Inc; Auburn, Calif.). To activate cells, 1 mL of isolated cells (density of $3\times10^6$ cells/mL) can be cultured in AIM V media for 3 days (Life Technologies; Carlsbad, Calif.) in a standard 24-well plate (BD; Franklin Lakes, N.J.) pre-coated with anti-CD3 and anti-CD28 antibodies (Affymetrix eBioscience, San Diego, Calif.). The pre-coating process can be carried out by adding 300 µL of carbonate buffer (0.1 M NaHCO3 (Sigma-Aldrich, St. Louis, Mo.), 0.5 M NaCl (Sigma-Aldrich), pH 8.3) containing 10 µg/mL anti-CD3 and 2 µg/mL anti-CD28 antibodies to each well, incubating for 2 hours at 37° C., and washing each well with AIM V media. Following the 3-day activation period, cells can be collected, counted, re-plated in 1 mL of AIM V media (density of $2\times10^6$ cells/mL) in a standard 24-well plate and treated with 100 ng/mL PEG-hIL-10 for 3 days. The process of activation and treatment with PEG-hIL-10 can be repeated, after which viable cells can be counted by Trypan Blue exclusion according to the manufacturer's protocol (Life Technologies).

Tumor Models and Tumor Analysis.

Any art-accepted tumor model, assay, and the like can be used to evaluate the effect of the IL-10 agents described herein on various tumors. The tumor models and tumor analyses described hereafter are representative of those that can be utilized. Syngeneic mouse tumor cells are injected subcutaneously or intradermally at $10^4$, $10^5$ or $10^6$ cells per tumor inoculation. Ep2 mammary carcinoma, CT26 colon carcinoma, PDV6 squamous carcinoma of the skin and 4T1 breast carcinoma models can be used (see, e.g., Langowski et al. (2006) Nature 442:461-465). Immunocompetent Balb/C or B-cell deficient Balb/C mice can be used. PEG 10-mIL-10 can be administered to the immunocompetent mice, while PEG-hIL-10 treatment can be in the B-cell deficient mice. Tumors are allowed to reach a size of 100-250 mm$^3$ before treatment is started. IL-10, PEG-mIL-10, PEG-hIL-10, or buffer control is administered SC at a site distant from the tumor implantation. Tumor growth is typically monitored twice weekly using electronic calipers. Tumor tissues and lymphatic organs are harvested at various endpoints to measure mRNA expression for a number of inflammatory markers and to perform immunohistochemistry for several inflammatory cell markers. The tissues are snap-frozen in liquid nitrogen and stored at −80° C. Primary tumor growth is typically monitored twice weekly using electronic calipers. Tumor volume can be calculated using the formula (width$^2$×length/2) where length is the longer dimension. Tumors are allowed to reach a size of 90-250 mm$^3$ before treatment is started.

Example 1

PEG-IL-10 Mediates CD8+ T Cell Immune Activation

The change in the number of PD-1- and LAG3-expressing CD8+ T cells was determined in cancer patients before and after 29 days of treatment with PEG-rHuIL-10. Two patients who responded to the therapy with a sustained partial response had an increase of the PD1+ CD8 T cells in the blood. The first patient (renal cell carcinoma) received 20 µg/kg PEG-rHuIL-10 SC daily and experienced a 71% reduction of total tumor burden after 22 weeks. The second patient (melanoma) received 40 µg/kg PEG-rHuIL-10 SC daily and experienced a 57% reduction of total tumor burden after 22 weeks.

Peripheral blood monocytic cells (PBMC) were isolated from the periphery of each patient pre-treatment and during the treatment period and were subjected to FACS analysis. As indicated in FIG. 1, the number of peripheral CD8+ T cells expressing PD-1 increased by ~2-fold within 29 days and continued to increase during the treatment period, and the number of peripheral CD8+ T cells expressing LAG3 increased by ~4-fold within 29 days. Both PD-1 and LAG3 are markers of CD8+ T cell activation and cytotoxic function. These findings suggest that PEG-rHuIL-10 administration mediated CD8+ T cell immune activation.

Example 2

PEG-IL-10 Enhances the Function of Activated Memory CD8+ T Cells

Memory T cells (also referred to as antigen-experienced T cells) are a subset of T lymphocytes (e.g., helper T cells (CD4+) and cytotoxic T cells (CD8+)) that have previously encountered and responded to their cognate antigen during prior infection, exposure to cancer, or previous vaccination. In contrast, naïve T cells have not encountered their cognate antigen within the periphery; they are commonly characterized by the absence of the activation markers CD25, CD44 or CD69, and the absence of memory CD45RO isoform. Memory T cells, which are generally CD45RO+, are able to reproduce and mount a faster and stronger immune response than naïve T cells.

Figure 2:
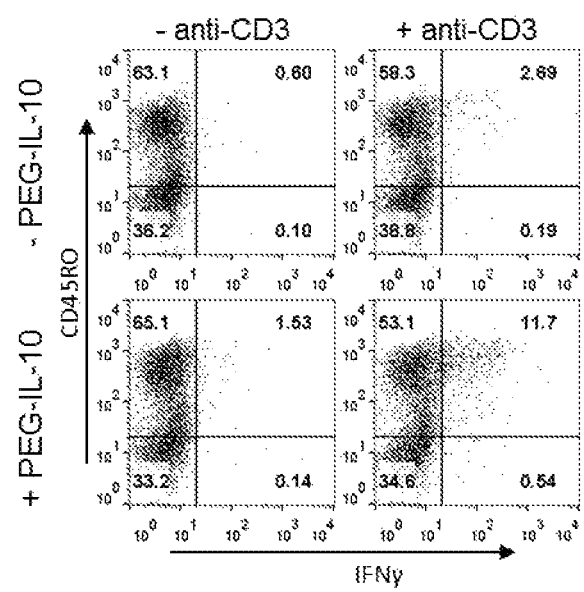
FIG. 2 indicates that PEG-IL-10 preferentially enhances IFNγ production in memory CD8+ T cells (CD45RO+) compared to naïve CD8+ T cells.

Given that CAR-T T cells are derived from memory CD8+ T cells, the effect of PEG-IL-10 on memory CD8+ T cells was assessed in vitro using standard methodology, an example of which is described herein. As indicated in FIG. 2, PEG-IL-10 preferentially enhances IFNγ production in memory CD8+ T cells (CD45RO+) and not naïve CD8+ T cells. These data are consistent with the effect of PEG-IL-10 to enhance the function of activated memory CD8+ T cells.

Example 3

PEG-IL-10 Treatment Results in a Greater Number of Activated Memory CD8+ T Cells As described herein, CAR-T cell therapy is derived from memory CD8+ T cells. In order to be effective, infused memory CD8+ T cells must not only exhibit cytotoxicity, but must also persist (Curran K J, Brentjens R J. (20 Apr. 2015) J Clin Oncol pii: JCO.2014.60.3449; Berger et al., (January 2008) J Clin Invest 118(1):294-305). However, repeated activation of T cells leads to activation-induced cell death, which decreases the number of cells and thus the overall therapeutic efficacy.

Figure 3:
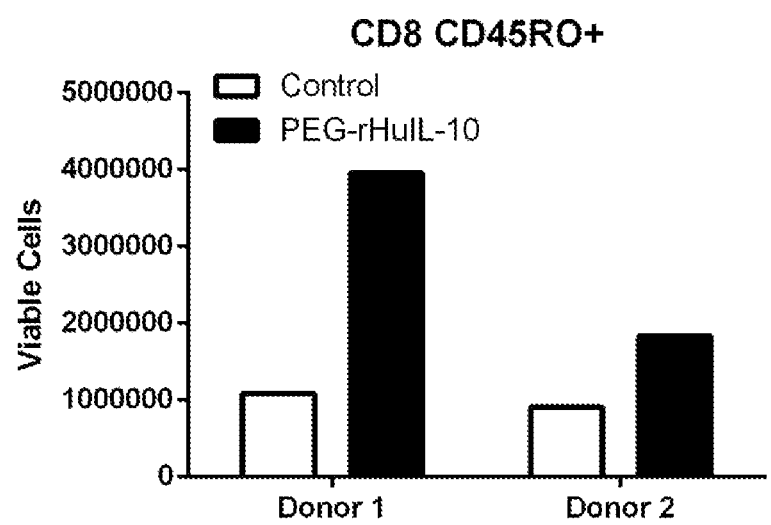
FIG. 3 indicates that PEG-IL-10 is capable of limiting activation-induced cell death in CD8+ T cells (CD45RO+).

Using the procedure described herein, the activation-induced cell death of human CD45RO+ memory CD8+ T cells from two donors was determined with and without treatment with PEG-IL-10. As indicated in FIG. 3, treatment of human CD45RO+ memory CD8+ T cells with PEG-IL-10 after two rounds of TCR and co-stimulation-induced activation resulted in a greater number of viable cells. These data indicate that PEG-IL-10 is capable of limiting activation-induced cell death, thus resulting in a greater number of activated memory T cells to persist. These observations suggest that the use of PEG-IL-10 in combination with CAR-T cell therapy provides additional clinical benefit.

Particular embodiments of this invention are described herein, including the best mode known to the inventors for carrying out the invention. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A method of modulating a T cell-mediated immune response to a target cell population expressing a cell surface antigen in a subject, comprising:
   a) administering to the subject a therapeutically effective amount of CD8+ T-cells genetically modified to express a chimeric antigen receptor (CAR T-cell), wherein the chimeric antigen receptor comprises:
      at least one antigen-specific targeting region that specifically binds a cell surface antigen present on the target cell population,
      a transmembrane domain, and
      an intracellular signaling domain, and
   b) administering to the subject a therapeutically effective amount of an IL-10 agent, wherein the IL-10 agent modulates T cell-mediated immune response to the target cell population.

2. The method of claim 1, wherein the intracellular signaling domain comprises a co-stimulatory domain.

3. The method of claim 1, wherein administration of the IL-10 agent to the subject is prior to administration of the therapeutically effective amount of CAR-T cells.

4. The method of claim 1, wherein administration of the IL-10 agent to the subject is simultaneously with administration of the therapeutically effective amount of CAR-T cells.

5. The method of claim 1, wherein administration of the IL-10 agent to the subject is subsequent to the administration of the therapeutically effective amount of CAR-T cells.

6. The method of claim 1, wherein the IL-10 agent is a PEG-IL-10.

7. The method of claim 6, wherein the PEG-IL-10 comprises at least one PEG molecule covalently attached to at least one amino acid residue of at least one monomer of IL-10.

8. The method of claim 6, wherein the PEG-IL-10 comprises a mixture of mono-pegylated and di-pegylated IL-10.

9. The method of claim 6, wherein the PEG component of the PEG-IL-10 has a molecular mass from 5 kDa to 30 kDa.

10. The method of claim 6, wherein the PEG component of the PEG-IL-10 has a molecular mass of at least 5 kDa.

11. The method of claim 6, wherein the PEG component of the PEG-IL-10 has a molecular mass of at least 20 kD.

12. The method of claim 1, wherein the IL-10 agent is administered subcutaneously.

13. The method of claim 1, wherein the amount of CD-8+ T-cells is obtained from the subject and genetically modified ex vivo.

14. The method of claim 1, wherein the target cell population comprises a tumor antigen.

15. The method of claim 14, wherein the tumor antigen is selected from the group consisting of CD19, CD20, CD22, ROR1, mesothelin, CD33/IL3Ra, c-Met, PSMA, Glycolipid F77, EGFRvIII, GD-2, NY-ESO-1 TCR, MAGE A3 TCR, or any combination thereof.

16. A method of treating a subject having a cancer-related disease, disorder or condition, comprising:
   a) administering to the subject a therapeutically effective amount of CD8+ T-cells genetically modified to express a chimeric antigen receptor (CAR T-cell), wherein the chimeric antigen receptor comprises
      at least one antigen-specific targeting region that specifically binds a cell surface tumor antigen present on a target tumor cell population,
      a transmembrane domain,
      an intracellular signaling domain, and
   b) administering to the subject a therapeutically effective amount of an IL-10 agent.

17. The method of claim 16, wherein the intracellular signaling domain comprises a co-stimulatory domain.

18. The method of claim 16, wherein administration of the IL-10 agent is prior to administration of the therapeutically effective amount of CAR-T cells.

19. The method of claim 16, wherein administration of the IL-10 agent is simultaneously with administration of the therapeutically effective amount of CAR-T cells.

20. The method of claim 16, wherein administration of the IL-10 agent is subsequent to the administration of the therapeutically effective amount of CAR-T cells.

21. The method of claim 16, wherein the IL-10 agent is a PEG-IL-10.

22. The method of claim 21, wherein the PEG-IL-10 comprises at least one PEG molecule covalently attached to at least one amino acid residue of at least one monomer of IL-10.

23. The method of claim 21, wherein the PEG-IL-10 comprises a mixture of mono-pegylated and di-pegylated IL-10.

24. The method of claim 21, wherein the PEG component of the PEG-IL-10 has a molecular mass from 5 kDa to 30 kDa.

25. The method of claim 21, wherein the PEG component of the PEG-IL-10 has a molecular mass of at least 5 kDa.

26. The method of claim 21, wherein the PEG component of the PEG-IL-10 has a molecular mass of at least 20 kD.

27. The method of claim 16, wherein the IL-10 agent is administered subcutaneously.

28. The method of claim 16, wherein the CD-8+ T-cells are obtained from the subject and genetically modified ex vivo.

* * * * *

UNITED STATES PATENT AND TRADEMARK OFFICE
CERTIFICATE OF CORRECTION

PATENT NO. : 10,195,274 B2
APPLICATION NO. : 15/926118
DATED : February 5, 2019
INVENTOR(S) : John Brian Mumm and Ivan Ho Chan Page 1 of 1

It is certified that error appears in the above-identified patent and that said Letters Patent is hereby corrected as shown below:

On the Title Page

Item [56], Column 2, Line 5, delete "( Year:" and insert -- (Year: --, therefor.

In the Claims

Column 59, Line 57, Claim 11, delete "kD." and insert -- kDa. --, therefor.

Column 59, Line 60, Claim 13, delete "CD-8+" and insert -- CD8+ --, therefor.

Column 60, Line 58, Claim 26, delete "kD." and insert -- kDa. --, therefor.

Column 60, Line 61, Claim 28, delete "CD-8+" and insert -- CD8+ --, therefor.

Signed and Sealed this
Sixteenth Day of April, 2019

Andrei Iancu
*Director of the United States Patent and Trademark Office*

```
                       SEQUENCE LISTING

<160> NUMBER OF SEQ ID NOS: 19

<210> SEQ ID NO 1
<211> LENGTH: 11
<212> TYPE: PRT
<213> ORGANISM: Artificial Sequence
<220> FEATURE:
<223> OTHER INFORMATION: Synthetic nucleic acid

<400> SEQUENCE: 1

Tyr Gly Arg Lys Lys Arg Arg Gln Arg Arg Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic nucleic acid

<400> SEQUENCE: 2

Arg Arg Gln Arg Arg Thr Ser Lys Leu Met Lys Arg
1               5                   10

<210> SEQ ID NO 3
<211> LENGTH: 27
<212> TYPE: PRT
<213> ORGANISM: Artificial Sequence
<220> FEATURE:
<223> OTHER INFORMATION: Synthetic nucleic acid

<400> SEQUENCE: 3

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 4
<211> LENGTH: 33
<212> TYPE: PRT
<213> ORGANISM: Artificial Sequence
<220> FEATURE:
<223> OTHER INFORMATION: Synthetic nucleic acid

<400> SEQUENCE: 4

Lys Ala Leu Ala Trp Glu Ala Lys Leu Ala Lys Ala Leu Ala Lys Ala
1               5                   10                  15
```

Leu Ala Lys His Leu Ala Lys Ala Leu Ala Lys Ala Leu Lys Cys Glu
            20                  25                  30
Ala

<210> SEQ ID NO 5
<211> LENGTH: 16
<212> TYPE: PRT
<213> ORGANISM: Artificial Sequence
<220> FEATURE:
<223> OTHER INFORMATION: Synthetic nucleic acid

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: Synthetic nucleic acid

<400> SEQUENCE: 6

Arg Lys Lys Arg Arg Gln Arg Arg Arg
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic nucleic acid

<400> SEQUENCE: 7

Arg Lys Lys Arg Arg Gln Arg Arg
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic nucleic acid

<400> SEQUENCE: 8

Tyr Ala Arg Ala Ala Ala Arg Gln Ala Arg Ala
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic nucleic acid

<400> SEQUENCE: 9

Thr His Arg Leu Pro Arg Arg Arg Arg Arg Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic nucleic acid

```
<400> SEQUENCE: 10

Gly Gly Arg Arg Ala Arg Arg Arg Arg Arg
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Synthetic nucleic acid
<220> FEATURE:
<221> NAME/KEY: MISC_FEATURE
<222> LOCATION: (1)..(5)
<223> OTHER INFORMATION: This stretch of residues may be present 1 to 50
      times.
<220> FEATURE:
<221> NAME/KEY: MISC_FEATURE
<222> LOCATION: (5)..(5)
<223> OTHER INFORMATION: This residue may be present 1 to 20 times.

<400> SEQUENCE: 11

Gly Ser Gly Gly Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic nucleic acid
<220> FEATURE:
<221> NAME/KEY: MISC_FEATURE
<222> LOCATION: (1)..(1)
<223> OTHER INFORMATION: This residue may be present 1 to 20 times.
<220> FEATURE:
<221> NAME/KEY: MISC_FEATURE
<222> LOCATION: (1)..(5)
<223> OTHER INFORMATION: This stretch of residues may be present 1 to 20
      times.
<220> FEATURE:
<221> NAME/KEY: MISC_FEATURE
<222> LOCATION: (2)..(2)
<223> OTHER INFORMATION: This residue may be present 1 to 20 times.
<220> FEATURE:
<221> NAME/KEY: MISC_FEATURE
<222> LOCATION: (3)..(3)
<223> OTHER INFORMATION: This residue may be present 1 to 20 times.
<220> FEATURE:
<221> NAME/KEY: MISC_FEATURE
<222> LOCATION: (4)..(4)
<223> OTHER INFORMATION: This residue may be present 1 to 20 times.
<220> FEATURE:
<221> NAME/KEY: MISC_FEATURE
<222> LOCATION: (5)..(5)
<223> OTHER INFORMATION: This residue may be present 1 to 20 times.

<400> SEQUENCE: 12

Gly Ser Gly Ser Gly
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic nucleic acid
<220> FEATURE:
<221> NAME/KEY: MISC_FEATURE
<222> LOCATION: (1)..(4)
<223> OTHER INFORMATION: This stretch of residues may be present 1 to 50
      times.
<220> FEATURE:
<221> NAME/KEY: MISC_FEATURE
```

```
<222> LOCATION: (4)..(4)
<223> OTHER INFORMATION: This residue may be present 1 to 20 times.

<400> SEQUENCE: 13

Gly Gly Gly Ser
1

<210> SEQ ID NO 14
<211> LENGTH: 4
<212> TYPE: PRT
<213> ORGANISM: Artificial Sequence
<220> FEATURE:
<223> OTHER INFORMATION: Synthetic nucleic acid

<400> SEQUENCE: 14

Gly Gly Ser Gly
1

<210> SEQ ID NO 15
<211> LENGTH: 5
<212> TYPE: PRT
<213> ORGANISM: Artificial Sequence
<220> FEATURE:
<223> OTHER INFORMATION: Synthetic nucleic acid

<400> SEQUENCE: 15

Gly Gly Ser Gly Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic nucleic acid

<400> SEQUENCE: 16

Gly Ser Gly Gly Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic nucleic acid

<400> SEQUENCE: 17

Gly Gly Gly Ser Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic nucleic acid

<400> SEQUENCE: 18

Gly Ser Ser Ser Gly
1               5

<210> SEQ ID NO 19
<211> LENGTH: 5
<212> TYPE: PRT
<213> ORGANISM: Artificial Sequence
<220> FEATURE:
```

```
<223> OTHER INFORMATION: Synthetic nucleic acid
<220> FEATURE:
<221> NAME/KEY: MISC_FEATURE
<222> LOCATION: (1)..(5)
<223> OTHER INFORMATION: This stretch of residues may be present 1 to 50
      times.

<400> SEQUENCE: 19

Gly Gly Gly Gly Ser
1               5
```